US009145455B2

(12) United States Patent
Stanker et al.

(10) Patent No.: US 9,145,455 B2
(45) Date of Patent: Sep. 29, 2015

(54) HIGH-AFFINITY MONOCLONAL ANTIBODIES FOR BOTULINUM TOXIN TYPE B

(71) Applicant: The United States of America, as represented by the Secretary of Agriculture, Washington, DC (US)

(72) Inventors: Larry H. Stanker, Livermore, CA (US); Miles C. Scotcher, Castro Valley, CA (US); Luisa W. Cheng, San Francisco, CA (US); Robert M. Hnasko, Port Costa, CA (US); Jeffery A. McGarvey, San Francisco, CA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 14/518,472

(22) Filed: Oct. 20, 2014

(65) Prior Publication Data

US 2015/0152168 A1 Jun. 4, 2015

Related U.S. Application Data

(62) Division of application No. 13/243,835, filed on Sep. 23, 2011, now Pat. No. 8,900,824.

(60) Provisional application No. 61/388,477, filed on Sep. 30, 2010.

(51) Int. Cl.
*C07K 16/00* (2006.01)
*C07K 16/12* (2006.01)

(52) U.S. Cl.
CPC ......... *C07K 16/1282* (2013.01); *C07K 2317/14* (2013.01)

(58) Field of Classification Search
None
See application file for complete search history.

(56) References Cited

U.S. PATENT DOCUMENTS 8,900,824 B1 * 12/2014 Stanker et al. ............... 435/7.32

OTHER PUBLICATIONS

Scotcher, M. et al. (2010) Detection of Botulinum Neurotoxin Serotype B at Sub Mouse LD50 Levels by a Sandwich Immunoassay and its Application to Toxin Detection in Milk PLoS one 5(6)el 1047:1-10.*

* cited by examiner

*Primary Examiner* — Jennifer Graser
(74) *Attorney, Agent, or Firm* — John D. Fado; Howard V. Owens, Jr.

(57) ABSTRACT

High affinity antibodies for binding epitopes of BoNT/B and hybridomas that produce such antibodies are described. The antibodies may be used in a kit for detecting BoNT/B in a sample.

2 Claims, 6 Drawing Sheets

HIGH-AFFINITY MONOCLONAL ANTIBODIES FOR BOTULINUM TOXIN TYPE B

RELATED APPLICATIONS

This application is a division of U.S. application Ser. No. 13/243,835, filed Sep. 23, 2011, now U.S. Pat. No. 8,900,824, which claims priority from U.S. Provisional Patent Application Ser. No. 61/388,477, filed Sep. 30, 2010, the contents of which are incorporated herein by reference in their entirety.

FIELD OF THE INVENTION

The present invention relates to high affinity monoclonal antibodies (Mab's) that bind to heavy and light chains of *Clostridium botulinum* neurotoxin (BoNT) and the associated use of these Mab's in detecting *Clostridium botulinum.*

BACKGROUND OF THE INVENTION

Foodborne botulism is a serious condition in which the patient experiences a gradual flaccid paralysis, 18 to 36 hours following consumption of contaminated food. If untreated, botulism can be fatal. Treatment is a lengthy process that may require hospitalization for several months with continuous mechanical ventilation (CDC, 1998, Dembek et al, 2007).

Botulinum neurotoxins (BoNTs) are the causative agents of botulism, and are the most potent naturally-occurring toxins known (Lamanna, 1959). There are seven serotypes of BoNTs, designated A through G, with serotypes A, B, E and F most frequently associated with human cases of botulism (Hatheway, 1990). BoNT/A is the most widely studied and best characterized of the BoNT serotypes—a cursory survey of the scientific literature indicates that there are approximately three times as many publications about BoNT/A than the next most frequent serotype, BoNT/B.

In the United States from 2001 to 2007, a total of 139 cases of foodborne botulism were reported to the Centers for Disease Control and Prevention (CDC). The majority of these cases were caused by intoxication by BoNT/A (76 cases) or BoNT/E (46 cases), with only 10 cases directly linked to consumption of food contaminated with BoNT/B. However, in the same seven years, BoNT/B was the causative agent of 387 of the 663 cases of infant botulism (58.4%) recorded by the CDC (National Botulism Surveillance, 2001-2007).

Although BoNT/B is a less frequently observed cause of foodborne botulism, it is nonetheless a significant threat to food safety. The largest recorded outbreaks of foodborne botulism to occur in both the United States and United Kingdom (UK) were attributed to the consumption of food contaminated with BoNT/B. In April 1977 in Michigan, a total of 59 patients were diagnosed with type B botulism, caused by eating a sauce made from improperly home-canned jalapenos. Eleven of the patients required hospitalization, although there were no reported deaths (Terranova et al., 1978). In June 1989 in the UK, 27 patients were intoxicated (one of whom died) by BoNT/B-contaminated hazelnut yoghurt (O'Mahony et al., 1990).

At the molecular level, BoNT/A and BoNT/B function in a similar manner. Both toxins are comprised of a 100 kDa heavy chain (Hc) and a 50 kDa light chain (Lc), linked by a single disulphide bond. The Hc functions by binding nerve cells and facilitates the internalization of the Lc, a zinc metalloprotease, into the pre-synaptic neuron at the neuromuscular junction (Montecucco & Schiavo, 1994; Simpson 2004). The Lc of BoNT/A cleaves synaptosomal-associated protein 25 (SNAP-25) whereas the Lc of BoNT/B cleaves synaptobrevin-2 (Schiavo et al., 1992; Blasi et al., 1993). Either cleavage event prevents the docking of acetylcholine-carrying vesicles with the presynaptic membrane, thus blocking the release of the neurotransmitter into the neuromuscular junction and ultimately prohibiting the contraction of the muscle (Simpson, 2004).

The development of a sensitive sandwich ELISA for the detection of BoNT/A, with a detection limit of 2 pg/mL was recently reported (Stanker et al., 2008). The mAbs (F1-2, F1-5 and F1-40) that form the foundation of this sandwich ELISA have been extensively characterized. Binding of these antibodies to the other serotypes of BoNT was undetectable (Stanker et al., 2008; Scotcher et al., 2009a & b). Whilst these studies have allowed the development of a test specific for BoNT/A, it is now necessary to develop a novel collection of mAbs to facilitate the development of a sandwich ELISA-based test specific to BoNT/B.

SUMMARY OF THE INVENTION

Herein is described the production and characterization of a collection of monoclonal antibodies (Mab's) specific to BoNT/B.

An embodiment of the invention is the development of a new sandwich ELISA, capable of detecting BoNT/B in buffer at concentrations undetectable by the mouse bioassay.

Another embodiment is the use of the sandwich ELISA to recover BoNT/B from spiked milk samples with minimal sample preparation or modification.

A further embodiment of the invention is the use of the monoclonal antibodies for in vivo treatment of exposure or infection to *Clostridium botulinum* neurotoxin (BoNT/B) or to serve as a vaccine or therapeutic agent wherein protection may be afforded via administration of the antibodies to those at risk of exposure or wherein infection or presence of the toxin within the organism has been detected.

STATEMENT OF DEPOSIT

Figure 1:
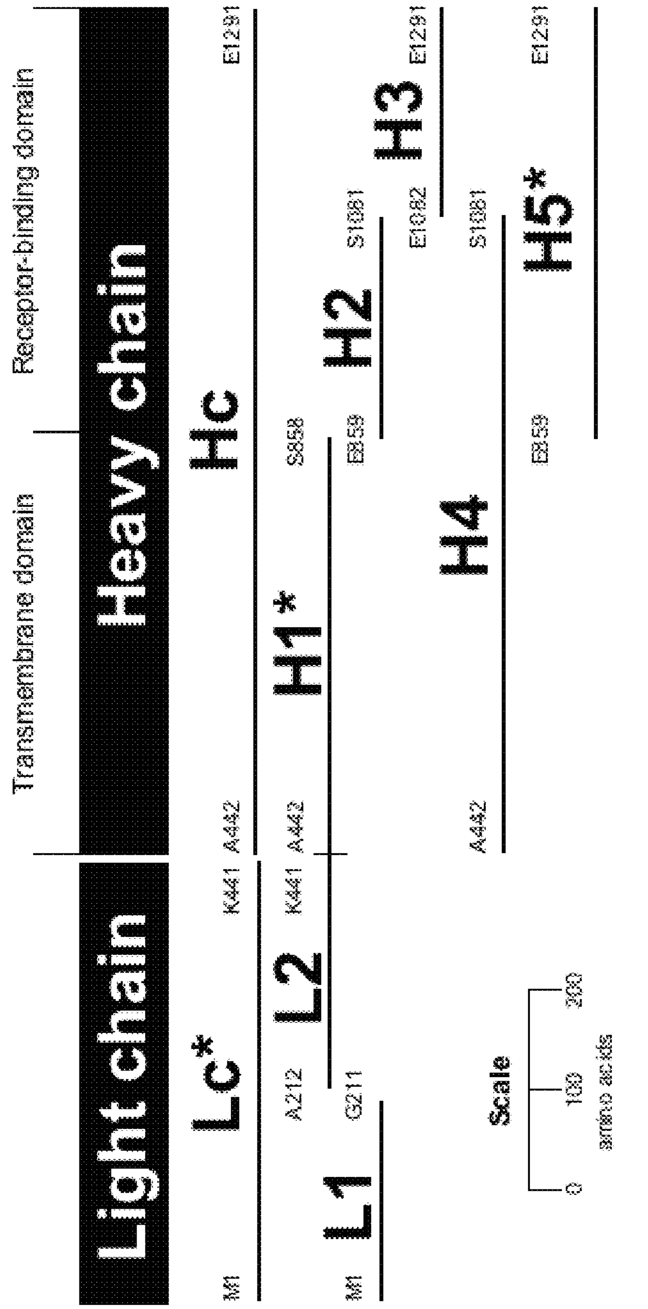
FIG. 1 is a representation of the transmembrane domain and receptor binding domain of BONT/B.

Monoclonal antibodies (Mab) to *Clostridium botulinum* neurotoxin were deposited May 5, 2011 under terms of the Budapest Treaty with the American Tissue Culture Collection (ATCC) P.O. Box 1549, Manassas, Va., 20108, USA. The Mab MCS 6-27-1-7 is produced by the hybridoma deposited under American Type Culture Collection (ATCC) Accession No. PTA-11871 and recognizes BoNT/B and BoNT/B Hc. Mab MCS 92-32-1-10 is produced by the hybridoma deposited under American Type Culture Collection (ATCC) Accession No. PTA-11872 and recognizes BoNT/B and BoNT/B Hc The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any Mab having the identifying characteristics of PTA-11871 and PTA-11872 including subcultures and variants thereof which have the identifying characteristics and activity as described herein are included.

DESCRIPTION OF THE INVENTION

The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement.

*Clostridium botulinum*, an anaerobic spore-forming bacterium, produces a family of botulinum neurotoxins (BoNT, EC 3.4.24.69) [Gill, M. Microbiol. Rev. 46:86-94 (1982)] consisting of seven serotypes, A-G (BoNT/A-BoNT/G). These are considered the most toxic proteins known. Serotype A is synthesized as a single 1,296 amino acid polypeptide, 150,000~Daltons (Da) that is then cleaved endogenously or exogenously forming a dichain molecule comprised of an ~100 kDa heavy chain (Hc) and an ~50 kDa light chain (Lc) linked by a single disulfide bond [Montecucco, C, and Schiavo, G. Structure and function of tetanus and botulinum neurotoxins. Quarterly Rev. Biophys. 28:423-472 (1995)]. The HC mediates toxin entry into neurons, and the Lc functions as a zinc-dependent endoprotease cleaving SNAR proteins involved in acetylcholine release resulting in muscular paralysis [Turton, K., Chaddock, J. A., Acharya, K. R. Trends Biochem. Sci. 27:552-558 (2002)]. The crystal structure of BoNT/A was determined at 3.3 Å resolution [Lacyt, D. B., Tepp, W., Cohen, A. C., DasGupta, B. R., and Stevens, R. C. Crystal structure of botulinum neurotoxin type A and implications for toxicity Nature Structural Biol. 5:898-902 (1998)].

An embodiment of the invention describes high affinity monoclonal antibodies (Mab's) to heavy and light chains of *Clostridium botulinum* neurotoxin B. The antibodies are $IgG_1$ subclass Mab's with kappa light chains that specifically bind BoNT serotype B (BoNT/B). Further characterization of these Mab's and their application to rapid immunoassay formats is presented.

A further embodiment of the invention describes the use of the Mab's in a test kit for the detection of *Clostridium botulinum*. Using the above test, toxin can be detected in amounts less than that detected by the mouse bioassay.

The term "antibody" (Ab) or "monoclonal antibody" (Mab) as used herein is meant to include intact molecules as well as fragments thereof (such as, for example, Fab and F(ab').sub.2 fragments) which are capable of binding. The language "monoclonal antibody" is art-recognized terminology. The monoclonal antibodies of the present invention can be prepared using classical cloning and cell fusion techniques. The immunogen (antigen) of interest, e.g. intact 150 kDa toxin, separated heavy or light chains of BoNT/A, or fragments of the Hc and Lc generated using recombinant methods expressed as toxin fragments or toxin fragments fusion proteins, is typically administered (e.g. intraperitoneal injection to wild-type mice or transgenic mice which produce desired antibodies, such as human antibodies, rats, rabbits or other animal species which can produce native or human antibodies. The immunogen can be administered alone or as a fusion protein to induce an immune response. Fusion proteins comprise the peptide against which an immune response is desired coupled to a carrier protein, such as .beta.-galactosidase, glutathione S-transferase, keyhole limpet hemocyanin (KLH), and bovine serum albumin, to name a few. In these cases, the peptides serve as haptens with the carrier proteins. After the animal is boosted, for example, three or four times, the spleen is removed and splenocytes are extracted and fused with myeloma cells using the well-known processes of Kohler and Milstein (Nature 256: 495-497 (1975)) and Harlow and Lane (Antibodies: A Laboratory Manual (Cold Spring Harbor Laboratory, New York 1988)). The resulting hybrid cells are then cloned in the conventional manner, e.g. using limiting dilution, screened and the resulting positive clones, which produce the desired monoclonal antibodies, cultured.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, chromogenic labels, fluorescent labels, and chemiluminescent labels [Harlow and Lane, Antibodies: A Laboratory Manual (Cold Spring Harbor Laboratory, New York 1988) 555-612].

The present invention still further pertains to a method for detecting BoNT/B in a sample containing BoNT/B. The method includes contacting the sample with an antibody which binds an epitope of BoNT/B, allowing the antibody to bind to BoNT/B to form an immunological complex, and detecting the formation of the immunological complex and correlating presence or absence of the immunological complex with presence or absence of BoNT/B in the sample. The sample can be biological, environmental or a food sample.

The language "detecting the formation of the immunological complex" is intended to include discovery of the presence or absence of BoNT/B in a sample. The presence or absence of BoNT/B can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988) 555-612. Such immunoassays include antibody capture assays, antigen capture assays, two-antibody sandwich assays, and immunoaffinity assays. These assays are commonly used by those of ordinary skill in the art. In an antibody capture assay, the antigen is attached to a solid support, and labeled antibody is allowed to bind. After washing, the assay is quantitated by measuring the amount of antibody retained on the solid support.

A variation of this assay is a competitive ELISA—as represented by an embodiment of the invention—wherein the antigen is bound to the solid support and two solutions containing antibodies which bind the antigen, for example, serum from a BoNT/B vaccine, and a monoclonal antibody of the present invention, are allowed to compete for binding of the antigen. The amount of monoclonal bound is then measured, and a determination is made whether the serum contains anti BoNT/B antibodies wherein detection of large amounts of monoclonal antibody indicates a small to no antibody against BoNT/A in the serum. This competitive ELISA can be used to predict immunity in a vaccine following vaccination.

Recombinant GST-fusion peptides of BoNT/A for the successful identification of the epitope sites of mAbs F1-2, F1-5 and F1-40, high affinity mAbs that bind BoNT/A were previously used. These studies demonstrated that recombinant peptides of BoNT/A could be successfully employed as surrogates for the BoNT/A holotoxin (Scotcher et al., 2009a & b). Based upon this observation, three recombinant GST-BoNT/B fusion peptides (Lc, H1, H5) were produced for immunizing mice in order to produce mAbs that bind wild type, intact BoNT/B. It was reasoned that the fusion peptides would not be toxic to the mice, and also would allow the production and identification of mAbs that bind specifically to the light chain (Lc), to the transmembrane domain (H1) and to the receptor-binding domain (H5) of BoNT/B (see FIG. 1).

Two mAbs that bound BoNT/B Lc (F24-1 and F27-33) and seven mAbs that bound the receptor-binding domain of the Hc (F26-16, F29-40, MCS 90-1-5-1, MCS 90-21-9-2, MCS 92-93-237, MCS 92-32-10-1 and MCS6-27) are disclosed. No mAbs that bound the transmembrane domain of Hc were identified. The Hc of mAb F26-16 was found to be an IgA isotype, whereas the Hc of the other eight mAbs were IgG isotypes. All nine mAbs exhibited kappa light chains.

Binding of each mAb to the collection of BoNT/B GST-fusion peptides shown in FIG. 1 was investigated by direct-binding ELISA. Each purified mAb bound the GST-fusion peptide used as an antigen to produce it, but not to any other GST-fusion peptide of BoNT/B. By using smaller GST-fusion peptides, the epitope location for each mAb could be localized to several hundred amino acids.

Both mAbs F24-1 and F27-33 bound the Lc of BoNT/B between residues A212 and K441. MAbs F26-16 and F1-40 bound the receptor-binding domain of the Hc, between E1082 and E1291. The epitope of mAb MCS6-27 could not be further defined because it failed to bind either smaller subpeptides (H2, H3) of the receptor-binding domain (H5). Since peptides H2 and H3 divide the receptor-binding domain, we speculated that mAb MCS6-27 might bind a region spanning between these two peptides. To test this hypothesis, we constructed a small synthetic peptide 20-mer (EERYKIQSYSEYLKDFWGNP) (SEQ ID NO: 56) corresponding to the amino acid sequence spanning peptides H2 and H3. However, no binding to this peptide was observed (data not shown). It is possible that MCS6-27 binds a discontinous conformational epitope that is not entirely present on peptides H2 or H3, or the short synthetic peptide tested. It can only be concluded that the epitope for MCS6-27 lies between amino acids E859 and E1291 of BoNT/B. MAbs MCS 90-1-5-1, MCS 90-21-9-2, MCS 92-93-237, MCS 92-32-10-1 bind the HC recombinant peptide HcP5 corresponding to the receptor binding domain.

Clustal W2 alignment amino acid sequence of the variable regions of anti-BoNT/B monoclonal antibodies are set forth in Table 3. Joining segments indicated with box. Constant region of kappa light chain and C1 region of heavy chain in bold. The binding of the nine mAbs to the BoNT/B holotoxin was confirmed by Western blot analysis shown in FIG. 2. All nine mAbs bound the intact BoNT/B holotoxin, with F24-1 and F27-33 selectively binding the Lc of reduced BoNT/B, and F26-16, F29-40 and MCS6-27, MCS 90-1-5-1, MCS 90-21-9-2, MCS 92-93-237, and MCS 92-32-10-1 binding the Hc of reduced BoNT/B. In order to visualize binding of MCS6-27 to the nitrocellulose-immobilized BoNT/B, the exposure time was increased to two hours, six times greater than that required for the other mAbs. This observation suggests that MCS6-27 binds poorly to the BoNT/B under these conditions, possibly because nitrocellulose-immobilized BoNT/B is in a conformation that is not optimal for the binding of mAb MCS6-27.

Figure 3:
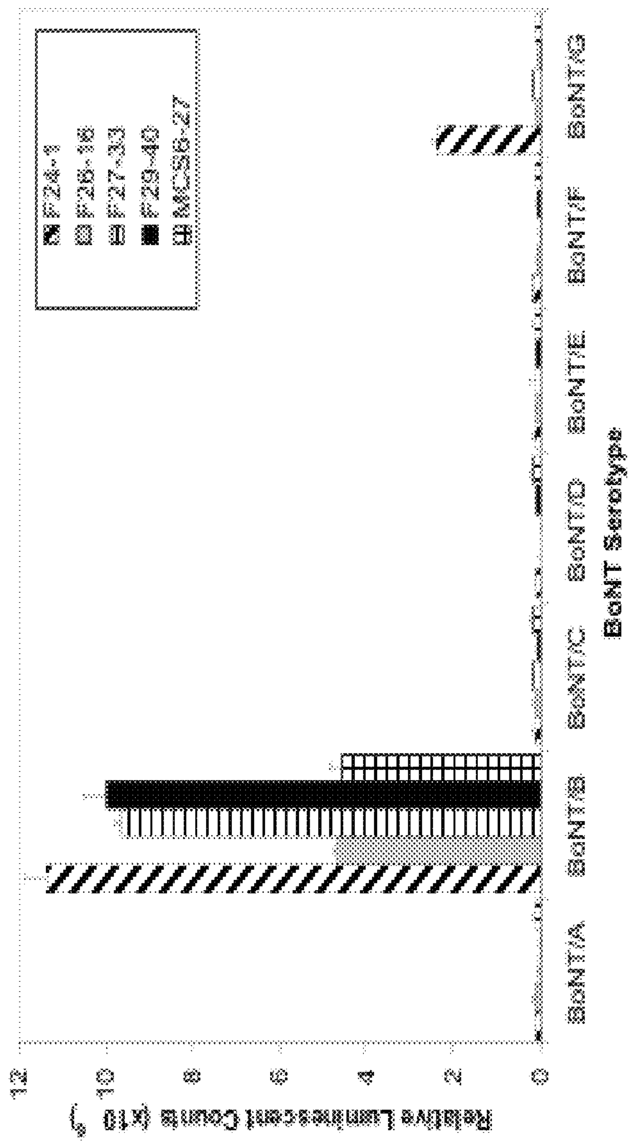
FIG. 3 is a graph of a luminescent assay of the binding of the Mab's to the seven serotypes of *Clostridium Botulinum.*

All of the mAbs except F24-1 bound only to BoNT/B. In contrast, mAb F24-1 bound to plate-immobilized BoNT/G at approximately 20% the intensity of binding to BoNT/B (FIG. 3). A comparison between the BoNT/B Lc between A212 and K441, and the corresponding region of the Lc of BoNT/G (Campbell et al., 1993) revealed 64% identity and 92% similarity in the amino acid sequence, suggesting that some identical or similar residues that comprise the epitope in BoNT/B are also present in BoNT/G.

The mAbs identified via the two different screening strategies displayed markedly different properties. None of the mAbs identified via the traditional direct-binding ELISA were able to capture BoNT/B from solution in the absence of SDS. Conversely, MCS 6-27, MCS 90-1-5-1, MCS 90-21-9-2, MCS 92-93-237, MCS 92-32-10-1 the only mABs identified via the capture-capture ELISA, were found to be excellent capture antibodies in the absence of SDS. Furthermore, a prophylactic, intravenous (iv) injection of 40 μg of mAb MCS6-27, 2.5 μg of mAb MCS 90-1-5-1, 40 μg of mAb MCS 90-21-9-2, 0.625 μg of MCS 92-23-23-7 and 40 μg of MCS 92-32-10-1 per mouse protected 100% of the mice studied from death or any symptoms of intoxication from an iv injection of 460 pg (100 mouse iv $LD_{50}$) of BoNT/B, consistent with the observation that these could bind BoNT/B in vitro under physiological conditions. The ratio of antibody to $LD_{50}$ units of BoNT/B toxin neutralized ranged from 0.2 to 0.003 μg mAb per 1 $LD_{50}$ unit. A study into the neutralization of BoNT/A in mice using mAb F1-2 revealed a ratio of 0.14 μg F1-2 per 1 $LD_{50}$ unit of BoNT/A (Cheng et al., 2009). It is possible that a lower quantity of mAb MCS6-27 and MCS 92-32-10-1 are sufficient to neutralize 1 $LD_{50}$ unit of BoNT/B, and is the subject of future studies. We hypothesize that since mAbs F24-1, F26-16, F27-33 and F29-40 were unable to bind BoNT/B in physiological buffer, they did not bind toxin in vivo and thus failed to protect mice from the neurotoxic effects of BoNT/B. The ability of a mAb to capture antigen from solution appears to be an indicator for toxin neutralization potential. Our data suggest that a capture-capture screen would be more appropriate than a direct binding ELISA if mAbs that neutralize toxin are to be identified.

The observation that all of the mAbs isolated using the direct binding ELISA screen gave strong ELISA titration curves but failed to bind toxin from solution suggested to us that immobilization of toxin on the microtiter plates results in an alteration of some physicochemical properties (e.g., surface charge or tertiary structure) so that a cryptic epitope is exposed that is not available when the toxin is in solution under physiological conditions. MAb MCS 6-27, MCS 90-1-5-1, MCS 90-21-9-2, MCS 92-23-23-7, MCS 92-32-10-1 all of which captured toxin in solution and protected from toxin exposure in vivo must bind surface epitopes not altered by immobilization in the wells of the microtiter plate. In an effort to clarify this possibility, we investigated the effects of two factors, the pH and SDS concentration of the capture buffer, on the ability of five of the mAbs to capture BoNT/B from solution. The effect of altering the pH was less marked than that of SDS, although both Lc-binding mAbs (F24-1, F27-33) displayed a greater sensitivity to alkaline pH than the other three Hc-binding mAbs (F26-16, F29-40 and MCS6-27). It is possible that the increasingly basic conditions greater than pH 6.0 affected the mAb or the toxin Lc in a manner that caused decreased binding. The same pH conditions did not affect the toxin Hc, or Hc-binding mAbs, in a way that decreased binding. However, in the absence of experiments that assay the structure of both antibody and toxin at each pH, this eventuality cannot be determined.

The concentration of SDS in the capture buffer had a dramatic effect on the ability of the mAbs to bind toxin in solution. SDS is often used at concentrations of 0.1% (~3.5 mM) in acrylamide gels and associated buffers to bind proteins and cause major conformational changes, commonly known as denaturation. However, there exists a dynamic range of SDS concentration at which SDS binds the protein and induces conformational changes that do not completely denature the protein. At lower concentrations, SDS monomers bind to certain high energy sites on the protein. As the concentration of SDS increases, SDS monomers bind in a cooperative manner ultimately resulting in the saturation of binding. (Robinson & Tanford, 1975; Bhuyan, 2009). It has been shown that the minimum concentration at which SDS can affect protein conformation is 0.1 mM, whereas some proteins can become 100% denatured at SDS concentrations of 1 mM (Reynolds & Tanford, 1970, Miyazawa et al., 1984). Thus, the effects SDS concentrations up to 1 mM on antibody capture were investigated.

Over the range of SDS concentrations investigated, the capture mAbs separated into two distinct groups, again mirroring the screen by which each mAb was identified. MAb MCS6-27 captured BoNT/B at SDS concentrations between 0 and 0.4 mM, whereas the mAbs F24-1, F27-33, F26-11 and F29-40 optimally captured toxin at SDS concentrations between 0.5 and 0.9 mM. A boundary between the two mAb populations fell at 0.4-0.5 mM SDS. We hypothesize that across the range of SDS concentrations from 0 to 1.0 mM, the SDS altered the protein conformation of either BoNT/B or the capture mAb in a manner that facilitated or inhibited binding. It is unlikely that either BoNT/B or MCS6-27 were completely denatured at 0.5 mM SDS, as the concentration of SDS seems too low to have that effect. However it is possible that the conformation of one or both proteins was altered sufficiently, or that key high energy sites on one or both proteins were blocked by monomeric SDS, resulting in the abolition of binding.

MAbs F24-1, F26-16, F27-33, F29-40, MCS6-27 MCS 92-23-23-7, MCS 92-32-10-1, MCS 90-1-5-1 and MCS 90-21-21-2 and the anti-BoNT/B rabbit and/or horse polyclonal were used in all combinations to identify capture and detector pairs for the development of a sandwich ELISA for BoNT/B detection. Using mAb F24-1 for capture and biotinylated F29-40 for detection, an SDS-dependent sandwich ELISA was constructed. However, the L.O.D. for this assay was approximately 90 pg/mL BoNT/B, almost two orders of magnitude higher than the L.O.D. of 1 pg/mL observed for the most sensitive sandwich ELISA that, under physiological conditions, used mAb MCS6-27 for capture and the anti-BoNT/B rabbit polyclonal antisera for detection. The L.O.Q. was determined to be approximately 2 pg/mL. Since 100 uL of sample is evaluated in the sandwich ELISA described here, the L.O.D. by mass of BoNT/B was 100 fg. The mouse $LD_{50}$ of the BoNT/B preparations used in our laboratory, when injected interperitoneally was found to be 8-10 pg per mouse (20 pg/mL). This sandwich ELISA is therefore approximately 50-fold more sensitive than the mouse bioassay for the detection of BoNT/B.

Monoclonal antibodies MCS 6-27, MCS 90-1-5-1, MCS 90-21-9-2, MCS 92-23-23-7, MCS 92-32-10-1 were evaluated to identify monoclonal-monoclonal capture detector pairs for development of a sandwich ELISA. An advantage of a monoclonal-monoclonal pair versus a monoclonal-polyclonal pair is the unlimited availability of highly consistent monoclonal antibodies for an assay ensuring greater assay stability and reproducibility over time. Using mAb MCS 6-27 as capture antibody and mAb biotinylated MCS 92-32-10-1 as detector an SDS-independent sandwich ELISA was constructed with an L.O.D. of 23 pg/mL (approximately equivalent to one mouse $LD_{50}$). The greater stability and reproducibility of a mAb/mAb sandwich ELISA make this a more desirable assay than the mAb/polyclonal assay described above.

We have previously described the development and application of a sandwich ELISA for the detection of BoNT/A in skim, 2% and whole milk. It was shown that good recoveries were observed when samples were spiked with as little as 312 pg/mL BoNT/A, but that defatting by centrifugation (14,000×g, 15 min, 6° C.) or a 10-fold dilution step was necessary to minimize sample interference (Stanker et al., 2008).

The monoclonal/polyclonal assay sandwich described here for the detection of BoNT/B in milk (skim, 2% and whole) does not require any defatting or dilution step. Toxin was readily detectable at a concentration of 39 pg/mL (3.9 pg by mass) in all three milk types, with recoveries of greater than 80%. Although the human oral $LD_{50}$ for BoNT/B has not been determined, the estimated human oral lethal dose (LD) for BoNT/A is 1 μg/kg body weight, or 70 μg for the average-sized human of 70 kg (Amon et al., 2001). Assuming a similar toxicity for BoNT/B, the sandwich ELISA can detect as little as ~1/1,800,000 of the human $LD_{50}$. Similarly, using the MCS 6-27/MCS92-32-10-1 sandwich ELISA BoNT/B was readily detected in milk without the need for defatting or other sample preparation. Toxin was readily detected in whole milk at a concentration of 2.4 pg/mL with recoveries greater than 104%. Thus, the mAb/mAb sandwich ELISA can detect as little as 1/1,000,000 of the human LD.

In an antigen capture assay, the antigen is attached to a solid support, and labeled antibody is allowed to bind. The unbound reactants are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen. These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes, enzymes or other reporter molecules such as microdots, nanoparticles, fluorochromes or electrochemical tags. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), Schurs, A. H. W. M., et al. 1977 (Clin. Chim Acta 81:1-40), Bobrovnik, S. A. 2003 (J. Biochem. Biochys. Methods 57:213-236), and Friguet et al 1985 (J. Immunol. Methods 77:305-319).

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, betagalactosidase, ribonuclease, urease, catalase, glucose-6-phosphate dehydrogenase, glucoamylase, acetylcholine esterase, etc.

Examples of suitable radioisotopic labels include .sup.3 H, .sup.125 I, .sup.131 I, .sup.32 P, .sup.35 S, .sup.14 C, .sup.51 Cr, .sup.57 To, .sup.58 Co, .sup.59 Fe, .sup.75 Se, .sup.152 Eu, .sup.90 Y, .sup.67 Cu, .sup.217 Ci, .sup.211 At, .sup.212 Pb, .sup.47 Sc, and .sup.109 Pd.

Examples of suitable fluorescent labels include an .sup.152 Eu label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent substrates include a luminal substrate, an isoluminal substrate, an aromatic acridinium ester substrate, an imidazole substrate, an acridinium salt substrate, an oxalate ester label, a luciferin substrate, a luciferase label, an aequorin label, etc.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid), agars, agarose, or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means known to one of skill in the art, including parenteral injection (such as intraperitoneal, subcutaneous, or intramuscular injection), orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestible liquid or solid formulation.

The treatment may be given in a single dose schedule, or preferably a multiple dose schedule in which a primary course of treatment may be with 1 or more separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 months and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

An embodiment of the invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

Materials and Methods

Construction, expression and purification of recombinant BoNT/B-GST fusion proteins Commercial enzymes (Phusion High-Fidelity DNA Polymerase, BamHI, XhoI, T4 polynucleotide kinase [3' phosphatase minus], T4 DNA ligase [New England BioLabs, Inc., Bethesda, Md.]) were used according to the manufacturer's recommendation. Primers used were purchased from Integrated DNA Technologies (Coralville, Iowa) and are shown in Table 1. Plasmid construction and manipulation was performed in *Escherichia coli* TOP10 cells (Invitrogen, Carlsbad, Calif.) grown aerobically in Luria-Bertani (LB) medium at 37° C. supplemented with 100 μg/mL ampicillin (Miller, 1972). Plasmids or DNA were purified using the QuickClean 5M range of kits (GenScript Corp., Piscataway, N.J.). All automated DNA sequencing was performed using the Big Dye Terminator Version 3.1 and XTerminator reagents, and a 3730 DNA Analyzer (Applied Biosystems, Foster City, Calif.).

Total genomic DNA from *Clostridium botulinum* (Strain Okra/Type B1), generously provided by Eric Johnson (University of Wisconsin, Madison Wis.), was used as a template to amplify the fragments of the light and heavy chains (Lc, L1, L2, Hc, H1, H2, H3, H4, H5,) using the primers indicated (see FIG. 1 and Table 1). Stop codons (TAA) were introduced when not present within the genomic DNA of the cloned region. All subsequent BoNT/B DNA fragments were cloned into plasmid pCR4-TOPO (Invitrogen) to allow sequencing using primers M13F and M13R. Additional primers (B-intseqF, B-intseqR) were required for the longest fragments, Hc and H1. The pCR4-derived plasmids were then digested using BamHI and XhoI, the BoNT/B fragment was purified and ligated into BamHI- and XhoI-digested pGS-21a (Genscript) to yield the correspondently named pGS plasmid (e.g. pGS-H1 for fragment H1). All pGS-21a-derived plasmids were sequenced using primer pGS-F and pGS-R, to confirm the correct integration of the BoNT/A fragment into the vector. The expression and purification of all GST-fusion proteins was performed as previously described (Scotcher et al., 2009a).

The recombinant DNA methods used in this study were approved by the Institutional Biosafety Committee. DNA sequences determined in this study have been deposited in GenBank and accession numbers are listed in Table 2.

TABLE 1

Primers

| Primer | Sequence | Constructs | SEQ ID NO: |
|---|---|---|---|
| B-LcF | GGATCCATGCCAGTTACAATAAATAATTTTAATTATAATG | Lc, L1 | SEQ ID NO: 40 |
| B-LcR | CTCGAG**TTA**TTTAACACTTTTACACATTTGTATCTTATATAC | Lc, L2 | SEQ ID NO: 41 |
| B-LcintF | GGATCCGCAAGTATATTTAATAGACG | L2 | SEQ ID NO: 42 |
| B-LcintR | CTCGAG**TTA**GCCTTTGTTTTCTTGAAC | L1 | SEQ ID NO: 43 |
| B-HcF | GGATCCGCTCCAGGAATATGTATTGATGTTG | Hc, H1, H4 | SEQ ID NO: 44 |
| B-HcR | CTCGAG**TTA**TTCAGTCCACCCTTCATCTTTAG | Hc, H3, H5 | SEQ ID NO: 45 |
| B-HcintR1 | CTCGAG**TTA**GCTATTATATTTATTAAACATTTC | H1 | SEQ ID NO: 46 |
| B-HcintF2 | GGATCCGAAATTTTAAATAATATTATCTTAAATTTAAG | H2, H5 | SEQ ID NO: 47 |
| B-HcintR2 | CTCGAG**TTA**GCTATATGATTGAATTTTATATC | H2, H4 | SEQ ID NO: 48 |
| B-HcintF3 | GGATCCGAATATTTAAAAGATTTTTGGGG | H3 | SEQ ID NO: 49 |
| M13F | GTAAAACGACGGCCAG | seq. pCR4 plsamids | SEQ ID NO: 50 |
| M13R | CAGGAAACAGCTATGAC | seq. pCR4 plasmids | SEQ ID NO: 51 |
| B-intseqF | CAATAGATAATGCTTTAACTAAAAGAAATG | seq. Hc,H1 | SEQ ID NO: 52 |
| B-intseqR | GTGTTCTATCTATATCACCATC | seq. Hc | SEQ ID NO: 53 |
| pGS-F | CAAATTGATAAGTACTTGAAATCC | seq. pGS-21a plasmids | SEQ ID NO: 54 |
| pGS-R | GCTAGTTATTGCTCAGAGG | seq. pGS-21a plasmids | SEQ ID NO: 55 |

TABLE 2

Characterization of monoclonal antibodies to BoNT/B

| Antibody | Screening method | Hc isotype | Peptides bound* | Epitope location | Accession # of Lc and Hc sequence |
|---|---|---|---|---|---|
| F24-1 | Direct binding | IgG1 | Lc, L2 | A212-K441 | Lc-GU799549<br>Hc-GU799550 |
| F24-4 | Direct binding | IgG1 | n/d | n/d | n/d |
| F26-16 | Direct binding | IgA | Hc, H3, H5 | E1082-E1291 | Lc-GU799551<br>Hc-GU799552 |
| F27-33 | Direct binding | IgG1 | Lc, L2 | A212-K441 | Lc-GU799553<br>Hc-GU799554 |
| F29-38 | Direct binding | IgM | n/d | n/d | n/d |
| F29-40 | Direct binding | IgG1 | Hc, H3, H5 | E1082-E1291 | Lc-GU799555<br>Hc-GU79556 |

TABLE 2-continued

Characterization of monoclonal antibodies to BoNT/B

| Antibody | Screening method | Hc isotype | Peptides bound* | Epitope location | Accession # of Lc and Hc sequence |
|---|---|---|---|---|---|
| MCS 6-27 | Capture-capture | IgG1 | Hc, H5 | E859-E1291 | Lc-GU79557<br>Hc-GU79558 |
| SS 90-21-9-2 | Cc | IgG1 | Hc, H5 | E859-E1291 | |
| SS 92-23-23-7 | Cc | IgG2b | Hc, H5 | E859-E1291 | |
| SS 92-32-10-1 | Cc | IgG1 | Hc, H5 | E859-E1291 | |
| SS 90-1-5-1 | Cc | IgG1 | Hc, H5 | E859-E1291 | |

Cc—Capture-capture

TABLE 3

Clustal W2 alignment amino acid sequence of the variable regions of anti-BoNT/B monoclonal antibodies.

Light Chains (Lc)

| Antibody | | FWR-1 CDR-1 FRW-2 CDR-2 FWR-3 | | |
|---|---|---|---|---|
| F24-1 | 1 | NIVMTQTPLSLPVSLGDQASISCRSSQSLVHS-NGNTYLHWYLQKPGQSPKLLIYKVSNRFSGVPDRFSGSGSGTDFT | 77 | SEQ ID NO: 1 |
| F26-16 | 1 | DIVMTQSPASLAVSLGQRATISCRASESVEYY--GTSLMQWFQQKPGQPPKVLIYAASNVESGVPARFSGSGSGTEFS | 76 | SEQ ID NO: 2 |
| F27-33 | 1 | DIVLTQSPSSLAVSVGEKVTMSCKSSQSLLYSSNQKNYLTWYQQKPGQSPKLLIYWASIRESGVPDRFTGSGSGTDFT | 78 | SEQ ID NO: 3 |
| F29-40 | 1 | DIVITQTPASLAVSLGQRATISCRASESINYY--GTNLLQWYQQKPGQPPKLLIYAASNVESGVPARFSGSGSGTDFS | 76 | SEQ ID NO: 4 |
| MCS6-27 | 1 | DIVLTQTPASLSVSVGETVTITCRASENIYSH------LAWYQQKQGKSPQLLVYTATNLADGVPSRFSGRGSGTQYS | 72 | SEQ ID NO: 5 |
| MCS92-23 | 1 | -----VTPFCI---CGRYVTITCRASQNIYSH------LTWFQQRQGRSPQLLVYTATNLADGVPARFSGSGSGTQYS | 63 | SEQ ID NO: 6 |
| MCS92-32 | 1 | -------HFSI-LSLWRSVSISCRTSQSLVNN-KGNTYLSWYLHKPGQSPQLLIYGISNRFSGVPDRFSGSGSGTDFT | 71 | SEQ ID NO: 7 |
| MCS90-1 | 1 | -------EPSLAVSLGQRATISCRASESVDSY--GNSFMHWYQQKPGQPPKLLIYRASNLQSGIPARFSGSGSRTDFT | 69 | SEQ ID NO: 8 |
| MCS90-21 | 1 | -------EPSLAVSLGQRATISCRASESVDSY--GNSFMHWYQQKPGQPPKLLIYRASNLQSGIPAR-SGSGSRTDFT | 69 | SEQ ID NO: 9 |

| | | FWR-3 CDR-3 FRW-4 Constant | | Joining Segment* | |
|---|---|---|---|---|---|
| F24-1 | 78 | LKISRVEAEDLGVYFCSQSTHVPYTFGGGTKLEIKR**ADAAPTVS** | 120 | J4 | SEQ ID NO: 10 |
| F26-16 | 78 | LNIHPVEEDDIAMYFCQQSRKVPYTFGGGTKLEIKR**ADAAPTVS** | 120 | J4 | SEQ ID NO: 11 |
| F27-33 | 79 | KIISSVKAEDLAVYYCHQYFGY-HTFGGGTKLEIKR**ADAAPTVS** | 121 | J4 | SEQ ID NO: 12 |
| F29-40 | 77 | LNIHPVEEDDIAMYFCQQSRKVPFTFGSGTRLEIKR**ADAAPTVS** | 120 | J2 | SEQ ID NO: 13 |
| MCS6-27 | 73 | LKINSLQSEDFGIYFCQHFWGTPWTFGGGTKLEIKR**ADAAPTVS** | 116 | J5 | SEQ ID NO: 14 |
| MCS92-23 | 64 | LKINNLQSEDFGTYYCQHFWGTPWTFGGGTKLEIKR**ADAAPTVS** | 106 | J5 | SEQ ID NO: 15 |
| MCS92-32 | 72 | LKISTIKPEDLGMYYCFQGTHQPFTFGAGTKLELKR**ADAAPTVS** | 116 | J1 | SEQ ID NO: 16 |
| MCS90-1 | 70 | LTINPVEADDVATYYCQQSNEDPHS-DRNRATNLKRTEM------- | 108 | | SEQ ID NO: 17 |
| MCS90-21 | 70 | LTINPVEADDVATYYCQQSNEDPHS-DRNRATNLKRTEM------- | 108 | | SEQ ID NO: 18 |

Heavy Chains (HC)

| Antibody | | FWR-1 CDR-1 FWR-2 CDR-2 | | |
|---|---|---|---|---|
| F24-1 | 1 | EVKLEESGGGLVKLGGSLKLSCAVSGFTFS--SYYMSWVRQTPEKRLELVAAIKSNGDNT | 58 | SEQ ID NO: 19 |
| F26-16 | 1 | QVQLQQPGAELVKPGASVKLSCKASGYIFT--NYWMHWVKQRPGQGLEWIGEINPTNGRT | 58 | SEQ ID NO: 20 |
| F27-33 | 1 | EVKLQESGAELMKPGASVKISCKATGYTFS--NYWIEWVKQRPGHGLEWIGEILPGSGST | 58 | SEQ ID NO: 21 |
| F29-40 | 1 | EVQLEESGPELVKPGTSVKISCKASGYSFT--GYIINWVMQSQGKTPEWIGRINPNNGDT | 58 | SEQ ID NO: 22 |
| MCS6-27 | 1 | EVQLEQSGPGLVKPSQSLSLTCTVTGYSITN-DYAWNWIRQFPGNKLEWMGYIN-YSGTT | 58 | SEQ ID NO: 23 |
| MCS90-1-5-1 | 1 | EVKLEESGAELVRPGTSVKMSCKAAGYTFT--NYWIGWVKERPGHGLEWIGDIFPGGGFT | 58 | SEQ ID NO: 24 |
| MCS92-32 | 1 | QVTLKESGPGVLQPSQTLSLTCSFSGFSLNTSNVVVNWIRQPSGKDLEWLAHIWWDNDKA | 60 | SEQ ID NO: 25 |

| | CDR-2 FWR-3 CDR-3 FWR-4 | | |
|---|---|---|---|
| F24-1 | YYSD-TVKGRFTISRDNAKNTLYLQMSSLKSEDTAFYYCARFN--SGSSWFDYWGQGTLV | 117 | SEQ ID NO: 26 |
| F26-16 | NQNE-KFKSKATLTVDKSSSTAHMQLSSLTSEDSAVYYCARRG-------FGNWGQGTTL | 112 | SEQ ID NO: 27 |
| F27-33 | NNNE-KFKGKATFTADSSSNTVYMQLSSLTSEDSAVYYCARLD------VMDYWGQGTSV | 113 | SEQ ID NO: 28 |
| F29-40 | SYNQ-KFKGKATLTVDRSSSTAHMEVRSLTSEDSAVYYCARTG-------FGYWGQGTLV | 112 | SEQ ID NO: 29 |
| MCS6-27 | SYNP-SLKSRISITRDTSKNQFFLQFNSVTTEDTATYYCARSP-------LAYWGQGTLV | 112 | SEQ ID NO: 30 |
| MCS90-1-5-1 | NYNE-NFKGKATLTADTSSSPAYMQLSSMTSEDSSIYHCARGRGHNSSTYFDSWGQGTTL | 119 | SEQ ID NO: 31 |
| MCS92-32 | YKSVXRGDXQFPRIPPATRYSSTSPMWTLRILPHTTVLECLXX-----HTLDYWGQGTSS | 114 | SEQ ID NO: 32 |
| | . . : . : . :: : . : ***** | | |

| | Constant | | Joining Segment | |
|---|---|---|---|---|
| F24-1 | TVSA**AKTTPPSVYR** | 131 | J3 | SEQ ID NO: 33 |
| F26-16 | TVSS**ESARNPTIR-** | 130 | J2 | SEQ ID NO: 34 |
| F27-33 | TVSS**AKTTPPSVYR** | 131 | J4 | SEQ ID NO: 35 |
| F29-40 | TVSA**AKTTPPSVYR** | 131 | J3 | SEQ ID NO: 36 |
| MCS6-27 | TVSA**AKTTPPSVYR** | 131 | J3 | SEQ ID NO: 37 |
| MCS90-1-5-1 | T-**SPA**---------- | 121 | J2 | SEQ ID NO: 38 |
| MCS92-32 | PSAQ----------- | 121 | J4 | SEQ ID NO: 39 |

Monoclonal Antibody Procedure

The method used for monoclonal antibody production has been described previously (Stanker et al., 2008). Significant differences from this method are described below.

Solutions of three peptide fragments at the concentrations indicated (Lc, 90 μg/mL; H1, 186 μg/mL; H5, 265 μg/mL) were mixed with Sigma Adjuvant System #S6322 according to manufacturer's instructions (Sigma-Aldrich, St. Louis, Mo.). Five female BALB/cJ mice (Simonsen Laboratories, Gilroy, Calif.) were immunized three times at 2-week intervals by intraperitoneal injection (i.p.) of 100 μL of each antigen-adjuvant solution. Two weeks after the third injection, serum was obtained from each mouse and evaluated for anti-BoNT/B antibodies via direct binding ELISA screens. Mice were injected i.p. with 2 μg of the appropriate peptide fragment in 0.01 M phosphate buffered saline (PBS; #P-3813, Sigma-Aldrich) three days prior to being euthanized and subjected to the fusion procedure.

Supernatants from cell fusion plates were subjected to screening either by direct binding ELISA or by capture-capture ELISA screens.

Screening Methods

Direct binding ELISA screens were performed as previously described (Stanker et al., 2008), using microtiter plates coated with 50 μL per well of a 0.1 μg/mL solution of BoNT/B (Strain Okra/Type B1, Metabiologics Incorporated, Madison Wis.) in 0.05M sodium carbonate buffer, pH 9.6. Binding was visualized using SuperSignal West Dura Extended Duration Substrate (Pierce, Rockford, Ill.) according to manufacturer's instructions. The plates were incubated for 3 min at room temperature and luminescent counts recorded using a Wallac Victor 2 Multilabel Counter (PerkinElmer Inc., Waltham, Mass.).

Capture-capture ELISA screens were performed as follows. Unless stated otherwise, 50 μL per well of all solutions were used. Microtiter plates were coated with a 1 μg/mL solution of goat anti-mouse IgG Fc gamma #AP127 (Millipore, Billerica Mass.) in 0.05 M sodium carbonate buffer, pH 9.6 overnight at 4° C. The IgG solution was aspirated and non-coated sites blocked by adding 300 μL per well of 3% non-fat dry milk in Tris-buffered saline containing 0.05% Tween-20 (NFDM-TBST) and the plates were incubated for 1 h at 37° C. The plates were washed once with 0.05% Tween-20, then cell culture supernatants were added and the plates were incubated at 37° C. for 1 h. The plates were washed three times with 0.05% Tween-20, then a solution of BoNT/B in NFDM-TBST (50 ng/mL) was added and the plates were incubated at 37° C. for 1 h. Plates were washed three times as before, then a 1 μg/mL solution of anti-BoNT/B rabbit polyclonal antibodies (Metabiologics) in NFDM-TBST was added and the plates were incubated at 37° C. for 1 h. Plates were washed three times as before, then a 1 μg/mL solution of goat anti-rabbit HRP-conjugated polyclonal antibodies #A6154 (Sigma-Aldrich) was added and the plates were incubated at 37° C. for 1 h. Plates were again washed three times, and binding was visualized as described above.

Cells from the wells giving positive signals for antibody production were cloned by limiting dilution. Hybridomas were then expanded and small amounts (usually less than 10 mL) of ascites fluids obtained (Covance Research Products, Inc., Denver, Pa.). Antibodies were purified by affinity chromatography on Protein-G (for IgG) or Protein L (for IgA) Sepharose. Bound antibody was eluted with 0.1 M glycine-HCl, pH 2.7. Protein concentrations were determined with a BCA-kit (Pierce) using the microplate method suggested by the manufacturer.

Antibody Isotyping, Western Blotting, Peptide Binding

All coating, blocking and washing steps of subsequent ELISAs were performed as described for the capture-capture ELISA screen, unless stated otherwise.

The isotype of each antibody was determined using the SBA Clonotyping System/HRP in ELISA format, according to manufacturer's instructions (Southern Biotech, Birmingham Ala.).

Western Blotting was performed as previously described (Stanker et al., 2008), except that BoNT/B was used instead of BoNT/A. BoNT/B was reduced by the addition of dithiothreitol (DTT) at a final concentration of 10 mM.

Basic characterization of the epitopes of each antibody was performed by direct binding ELISA. The wells of clear microtiter plates were coated with each of the BoNT/B GST-fusion proteins (see FIG. 1), incubated overnight at 4° C., blocked with NFDM-TBST and washed. Hybridoma supernatant, diluted 1:10 in NFDM-TBST, was added to each well and incubated for 1 h at 37° C. The plate was washed, then a 1 μg/mL solution of goat anti-mouse HRP-conjugated polyclonal antibodies #A4416 (Sigma-Aldrich) was added and the plates were incubated at 37° C. for 1 h. Plates were again washed three times, then K-Blue substrate (Neogen Corporation, Lexington, Ky.) was added (100 μL per well) and incubated with agitation for 5 min at room temperature. Stop solution (Neogen) was added (100 μL per well), and absorbance at 650 nm was measured using a VersaMax microplate reader (Molecular Devices, Sunnyvale Calif.). Each antibody was tested in triplicate.

Binding of Antibodies to BoNT Serotypes A Through G

Black microtiter plates were coated with the different serotypes of BoNT, A through G (Metabiologics) for direct binding ELISA analysis as described above. Purified anti-BoNT/B monoclonal antibody at a concentration of 10 μg/mL in NFDM-TBST was added to each BoNT serotype, and incubated for 1 h at 37° C. The plates were washed, then a 1 μg/mL solution of goat anti-mouse HRP-conjugated polyclonal antibodies #A4416 (Sigma-Aldrich) was added and the plates were incubated at 37° C. for 1 h. Plates were again washed three times, and binding was visualized using SuperSignal West Dura Extended Duration Substrate as described above. Each antibody was assayed against each serotype in triplicate.

Effects of pH and SDS on Capture of BoNT/B from Solution by mAbs

Black microtiter plates were coated with the anti-BoNT/B monoclonal antibodies at 10 μg/mL in 0.05 M sodium carbonate buffer, pH 9.6 overnight at 4° C. Non-coated sites were blocked by adding 300 μL per well of 3% non-fat dry milk in Tris buffered saline containing 0.05% Tween-20. Following incubation for 1 h at 37° C., plates were washed three times to remove any residual blocking agent. Solutions of BoNT/B in buffers of various pH and sodium dodecyl sulphate (SDS) concentrations were prepared on a deep-well (2 ml) 96-well plate. Phosphate-buffered saline was added to rows A through G to give a final pH (±0.1) of 5.5, 6.0, 6.5, 7.0, 7.5, 8.0, 8.5 and 9.0, respectively. SDS was added to columns 1 through 12 to give final concentrations of 0, 0.1, 0.2, 0.3, 0.4, 0.5, 0.6, 0.7, 0.8, 0.9, 1.0, 2.0 mM, respectively. The final concentration of BoNT/B was 100 ng/mL in all wells. The deep-well plate was gently agitated to mix the solutions, then 100 μL of each BoNT/B solution was pipetted into the corresponding well on the black microtiter plates. Following incubation for 1 h at 37° C., plates were subsequently treated in an identical manner to the capture-capture ELISA described earlier, using the anti-BoNT/B rabbit polyclonal antibodies, goat anti-rabbit HRP-conjugated polyclonal antibodies and SuperSignal West Dura Extended Duration Substrate to allow detection of BoNT/B capture. Each antibody was assayed in triplicate.

In vivo Neutralization of BoNT/B

Random groups of 10 mice (4-5 week old female Swiss Webster mice, 19-21 g; Charles River Laboratories, Portland Mich.) were injected intravenously (i.v.) into the lateral tail vein with 100 μL of mAbs diluted in PBS to a final dosage between 0.156 μg to 40 μg mAbs/mouse one hour prior to administration with 100 μL of BoNT/B holotoxin containing 1000 pg (200 mouse iv $LD_{50}$ units) diluted in phosphate gelatin buffer. Control mice were treated with 100 μL of PBS instead of mAbs. Mice were monitored closely over a 14 day period for any symptoms of intoxication, or death. Animal-use protocols were approved by the Animal Care and Use Committee of the USDA, Western Regional Research Center, Albany, Calif.

Cloning and Sequencing of Monoclonal Antibodies mRNA coding for the anti-BoNT/B monoclonal antibodies was extracted and purified from hybridoma cells as previously described (Scotcher et al., 2009a). mRNA was converted to cDNA, and the heavy and light chains of each antibody were amplified by PCR as previously described (Wang et al., 2000). The PCR products were gel-purified and treated with polynucleotide kinase (New England BioLabs). Circularized vector pCR2.1 (Invitrogen) was digested with EcoRV and treated with calf intestinal phosphatase (New England BioLabs). The PCR products were ligated into vector pCR2.1, transformed into TOP10 cells, then grown and prepared for DNA sequencing using primers M13F and M13R as described earlier.

Sandwich ELISA

All combinations of mAbs F24-1, F26-16, F27-33, F29-40, MCS6-27, SS 90-1-5-1, MCS 90-21-9-2, MCS 92-23-2-7, MCS 92-32-10-1 and the anti-BoNT/B rabbit polyclonal antibody were evaluated as capture and detector pairs for the development of a sandwich assay for BoNT/B detection. Detector mAbs (except the anti-BoNT/B rabbit polyclonal) were biotinylated using the EZ-Link Micro-Sulfo-NHS-Lc Biotinylation Kit (Thermo Scientific, Rockford Ill.), and then detected using Zymax streptavidin-HRP conjugate (Zymed, San Francisco Calif.). The anti-BoNT/B rabbit polyclonal binding was detected using goat anti-rabbit HRP-conjugated polyclonal described earlier (Sigma).

Three pairs of antibodies were identified: F24-1 (capture) and F29-40 (detector); MCS6-27 (capture) and the anti-BoNT/B rabbit polyclonal (detector); MCS6-27 (capture) and MCS 92-32-10-1 (detector). Binding conditions and solutions were optimized (data not shown) to yield the protocols described below. Unless stated otherwise, all solution volumes were 100 μL per well, all incubations were performed for 1 h at 37° C. with gentle agitation, and all washes were performed twelve times in water plus 0.05% Tween.

White microtiter plates were coated with mAbs F24-1 or MCS6-27 at a concentration of 5 μg/mL in 0.05 M sodium carbonate buffer, pH 9.6 overnight at 4° C. Non-coated sites were blocked by adding 300 μL per well of 5% non-fat dry milk in Tris buffered saline (pH 8.0) containing 0.05% Tween-20 (NFDM-TBST). Plates were incubated and washed as described above. BoNT/B was added to each plate at concentrations from 5000 to 0 pg/mL in a two-fold dilution series, in TBS pH 6.0 containing 0.6 mM sodium dodecyl sulphate (SDS) for the F24-1-coated plate, or in NFDM-TBST for the MCS6-27-coated plate. Plates were incubated and washed. Biotinylated mAb F29-40 was added to the F24-1-coated plate at a concentration of 5 μg/mL in TBS, pH 8.0 containing 0.6 mM SDS. The anti-BoNT/B rabbit polyclonal detector was diluted 2000-fold in NFDM-TBST and added to the MCS6-27-coated plate. Plates were incubated and washed. Zymax streptavidin-HRP conjugate was diluted 10,000-fold in TBS, pH 8.0 containing 0.6 mM SDS and added to the F24-1-coated plate. Next, goat anti-rabbit HRP-conjugated polyclonal antibody was diluted 2000-fold in NFDM-TBST and added to the MCS6-27-coated plate. Plates were incubated, washed then binding was visualized as described earlier.

Detection of BoNT/B in Milk Matrices

Both sandwich assays using MCS6-27 (capture) and the anti-BoNT/B rabbit polyclonal (detector) and MCS6-27 (capture) and MCS 92-32-10-1 (detector) were evaluated for their ability to detect BoNT/B in milk. The sandwich ELISA was performed as described above, with the exception of the capture stage which was performed as follows.

Three milk types (skim, 2% fat and whole) were spiked with BoNT/B at final concentrations of 10000, 5000, 2500, 1250, 625, 312, 156, 78 and 39 pg/mL. Several sample treatments were evaluated in order to defat the samples. Spiked milk samples were centrifuged at 14,000×g for 15 min at 6° C. Other samples were simply diluted in two-fold serial dilutions in blocking buffer (Stanker et al., 2008). Following defatting or serial dilution, 100 μL of sample was loaded onto the MCS6-27-coated microtiter plate and incubated for 1 h at 37° C. with gentle agitation. Recovery of BoNT/B from spiked milk samples is reported as a percentage of the recovery by comparison to a standard curve of BoNT/B spiked into NFDM-TBST Milk samples were analyzed in triplicate.

Characterization of Anti-BoNT/B Monoclonal Antibodies

A total of nine monoclonal antibodies (mAbs) were identified, cloned and characterized (Table 2). Six mAbs (F24-1, F24-4, F26-16, F27-33, F29-38, and F29-40) were identified using a traditional, direct binding ELISA screening method, and five mAb (MCS 6-27, MCS 90-1-5-1, MCS 90-21-9-2, MCS 92-23-23-7, MCS 92-32-10-1)) was identified using the capture-capture screen. Isotype analysis revealed that mAb F26-16 was an IgA, F29-38 was an IgM, MCS 92-23 was an IgG2b and the remaining eight mAbs were all IgG1s. All of the mAbs possessed kappa light chains.

Figure 2B:
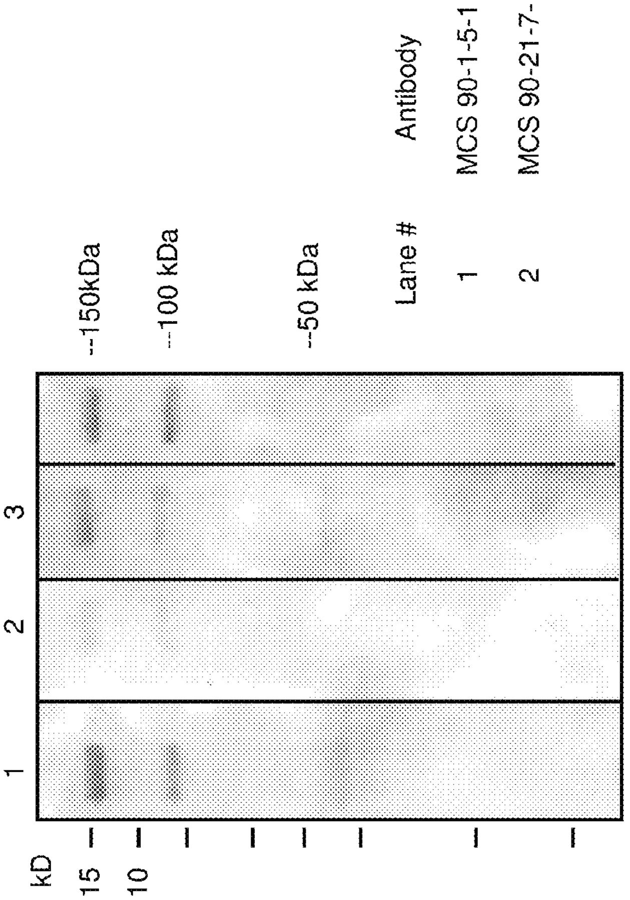
FIGS. 2A & 2B show the Western Blot of Mab's for the light chain—F24-1, F27-33; and heavy chain receptor domain mABs F26-16, F29-40, MCS6-27 MCS 90-1-5-1, MCS 90-21-9-2, MCS 92-23-23-7, and MCS 92-32-10-1.
Figure 2A:
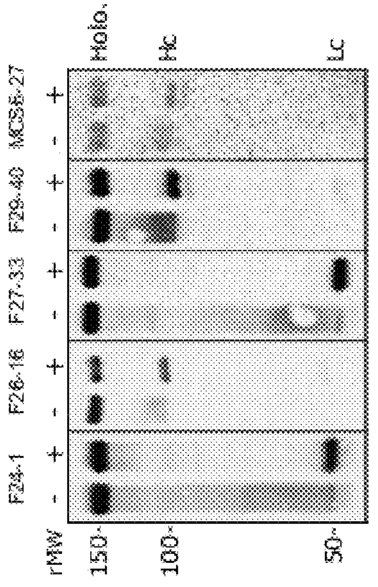

Compete sequences of the cloned cDNA coding for the heavy chain variable region was obtained for six mAbs, a partial sequence was obtained for one mAb, and no Hc sequence we obtained for two antibodies (see FIG. 2). The light chain sequences of of all nine antibodies was obtained. Sequence analysis revealed that mAbs F24-1 and F24-4 have identical sequences, and most likely represent independent fusions of a clonally-expanded population of lymphocytes. Each mAb possesses unique variable region sequences for their heavy and light chains, which can be accessed online via the Nucleotide Accession Numbers shown in Table 2. The leader sequences, framework regions, complementarity determining regions (CDRs) and J-regions were identified by inspecting the alignment of the mAb heavy and light chains to other antibody sequences (Morrison, 2002; Wood & Coleclough, 1984; Livesay & Subramaniam, 2004; Scotcher et al., 2009a, b).

Each antibody was studied in Western blot experiments, probing reduced and unreduced 150 kDa BoNT/B holotoxin following separation by SDS-PAGE (FIG. 3). In these experiments, a constant amount (μg) of each mAb was used to probe the Western blot. Exposure times of Western blots varied (FIG. 3A); mAbs F24-1, F26-16, F27-33 and F29-40 were exposed for 20 min, whereas the exposure time for MCS6-27 was 120 min. Constant exposure time of 10 min. was used for MCS 90-1-5-1, MCS 90-21-9-2, MCS 92-23-23-7 and MCS 92-32-10-1. All of the mAbs bound the 150 kDa BoNT/B holotoxin in the unreduced samples. Using reduced samples, mAbs F24-1 and F27-33 bound the BoNT/B Lc, and mAbs F26-16, F29-40, MCS6-27, MCS 90-1-5-1, MCSS 90-21-9-2, MCS 92-23-23-7 and MCS 92-32-10-1 bound the BoNT/B Hc. Binding to residual 150 kDa BoNT/B holotoxin was also observed in the reduced samples.

In an effort to more precisely define the binding epitopes for these mAbs, direct binding ELISA experiments were performed to identify which BoNT/B GST-fusion peptides each antibody bound (See FIG. 1 and Table 2, columns 4 & 5). MAbs F24-1 and F27-33 were both found to bind the Lc and L2 fragments, but not the L1 fragment or any of the other fragments derived from the BoNT/B heavy chain. The binding epitope for both mAbs is therefore localized to a 230 amino acid fragment of the BoNT/B light chain, between amino acids A212 and K441. MAbs F26-16 and F29-40 bound the Hc, H3 and H5 fragments, but not the Lc, L1, L2, H1, H2 or H4 fragments. The binding epitope for both mAbs is therefore localized to a 210 amino acid fragment of the BoNT/B heavy chain, between amino acids E1082 and E1291. In contrast, mAb MCS6-27, MCS 90-1-5-1, MCS 90-21-9-2, MCS 92-23-23-7 and MCS 92-32-10-1 bound fragments Hc and H5, but no binding to any other fragment was detected, indicating that the binding epitope is localized to a 433 amino acid fragment of the BoNT/B heavy chain, between amino acids E859 and E1291. These observations are consistent with the binding data obtained from the Western blot experiments described earlier.

Figure 4:
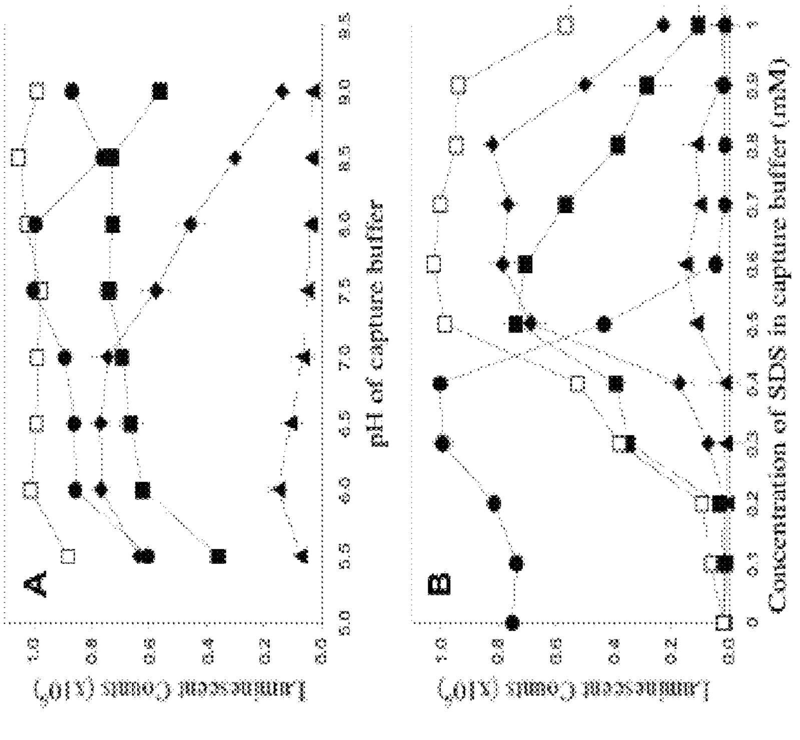
FIG. 4 is a graph of the effects of SDS concentration and pH on BoNT/B capture.

Direct binding ELISAs were performed to test whether each mAb would bind uniquely to BoNT/B, or whether binding to other BoNT serotypes could be detected. These data are summarized in FIG. 4. MAbs F26-16, F27-33, F29-40 and MCS6-27, MCS 90-1-5-1, MCS 90-21-9-2, MCS 92-23-23-7 and MCS 92-32-10-1 bound only BoNT serotype B, whereas mAb F24-1 bound BoNT serotype B and serotype G.

Effects of pH and SDS on Capture of BoNT/B in Solution by mAbs

The ability of each mAb to capture BoNT/B from solution was evaluated by sandwich ELISA. Plates were coated with the capture antibody, BoNT/B was applied (100 ng/mL in 1×TBS), and capture toxin was then detected using a rabbit anti-BoNT/B polyclonal antibody followed by an HRP-conjugated, goat anti-rabbit polyclonal antibody (see methods). Initial experiments indicated that only mAb MCS6-27, MCS 90-21, MCS 92-23, MCS 92-32 were able to capture BoNT/B from solution. BoNT/B was not detected using mAbs F24-1, F26-16, F27-33 or F29-40 as capture antibodies (data not shown). The effects of the pH and SDS concentration of the capture buffer were then evaluated for mAbs F24-1, F26-16, F27-33, F29-40 and MCS 6-27.

Figure 5B:
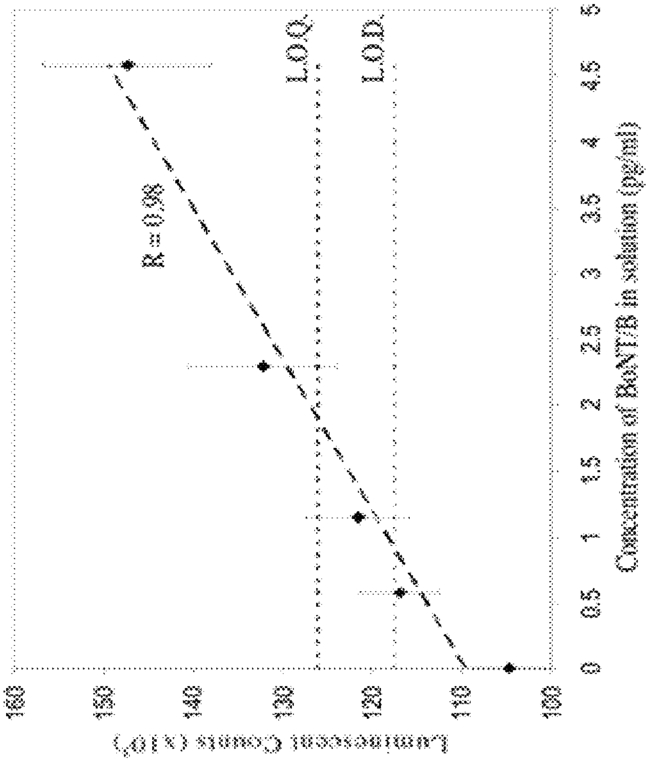
FIGS. 5A & 5B are graphs of Sandwich ELISA for detection of BoNT/B. Panel A, MAb MCS6-27 was used as capture antibody, Biotin labeled mAB MCS 92-32, 1-10 was used in conjunction with an HRP-conjugated streptavidin as detector. Panel B. mAb MCS6-27 was used as capture antibody and a polyclonal rabbit anti-toxin antibody used as the detector antibody.
Figure 5A:
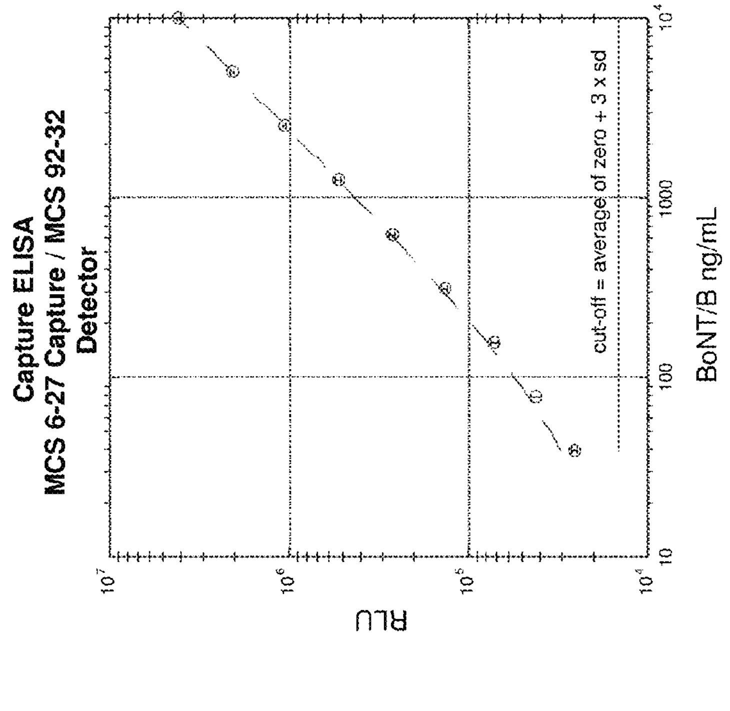

The effect of pH, ranging from 5.5 to 9.0, on the ability of the mAbs to capture BoNT/B from solution is summarized in FIG. 5A. For the Hc-binding mAbs F26-16, F29-40 and MCS6-27, the pH optimum for BoNT/B capture spanned a broad range from pH 6.0 to 8.5. For the Lc-binding mAbs F24-1 and F27-33, the pH optimum for BoNT/B capture was pH 6.0. It should be noted that in the absence of SDS, no BoNT/B captured by mAbs F24-1, F26-16, F27-33 and F29-40 was detected at any pH tested.

FIG. 5B shows the effect of SDS concentration, ranging from 0 to 2.0 mM, on the capture of BoNT/B at the optimal pH for each mAb. MCS6-27 captured BoNT/B at SDS concentrations of 0 to 0.4 mM, reaching an optimal point at 0.4 mM SDS then sharply decreasing such that at SDS concentrations higher than 0.6 mM, BoNT/B capture was not detected. Conversely, no BoNT/B captured by mAbs F24-1, F26-16, F27-33 and F29-40 was detected at 0 mM SDS, but captured BoNT/B was detected with increasing concentration of SDS up to approximately 0.5 mM. Each of these mAbs exhibited the greatest amount of BoNT/B captured at an SDS concentration between 0.5 and 0.8 mM. At SDS concentrations greater than 0.8 mM, the amount of BoNT/B captured declined sharply, with no captured BoNT/B detectable at SDS concentrations of 2 mM (not shown).

In vivo Neutralization of BoNT/B mAbs, F24-1, F26-16, F27-33, F29-40, MCS6-27, MCS 90-1-5-1, MCS 90-21-9-2, MCS 92-23-23-7 and MCS 92-32-10-1 were tested individually for their ability to neutralize BoNT/B holotoxin in a systemic mouse model of intoxication. One hour following intravenous (iv) administration of a mAb against BoNT/B, a lethal dose of BoNT/B (1000 pg/mouse or about 100 mouse iv $LD_{50}$) was delivered iv and the animals monitored over time. In the absence of mAbs, intoxicated mice treated with PBS alone died within 3.5-5.5 hrs. Mice pre-treated with 80 μg of F24-1, F26-16, F27-33 or F29-40 were not protected from death and had survival times similar to the PBS treated control mice. In contrast, pre-treatment with 40 μg of MCS6-27 and MCS 92-32-10-1 completely protected mice from death as well as any visible symptoms of botulism over the course of 14 days. Pre treatment with 2.5 μg of mAb MCS 90-1-5-1 and as little as 0.625 μg of MCS 92-23-23-7 completely protected mice.

Sandwich ELISA for BoNT/B Detection

Figure 6:
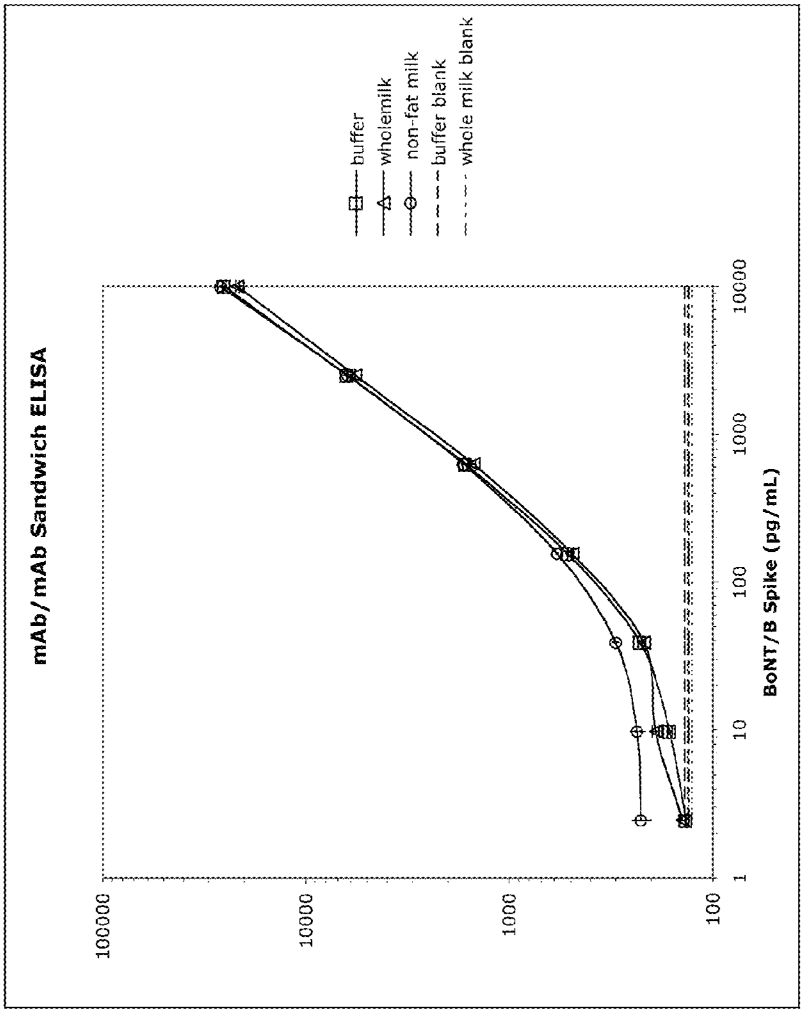
FIG. 6 is a graph of chemiluminescent Sandwich ELSA using MCS6-27 as capture antibody and biotin labeled mAb MCS 92-32-10-1 as detector antibody in conjunction with HdRP-conjugated Ruthinium as detector.

All combinations of mAbs F24-1, F26-16, F27-33, F29-40, MCS6-27, MCS 90-21, MCS 92-23, MCS 92-32 and the anti-BoNT/B polyclonal were evaluated as capture and detector pairs for the development of a sandwich assay for BoNT/B detection. The combination of MCS6-27 (capture) and rabbit/horse anti-BoNT/B polyclonal (detector) was found to be most sensitive, as shown in FIG. 6A. This ELISA exhibits a limit of detection (L.O.D., defined as 3 standard deviations above the zero) of approximately 1 pg/mL BoNT/B, and a limit of quantitation (L.O.Q., defined as 5 standard deviations above the zero) of approximately 2 pg/mL BoNT/B. A correlation coefficient (R) value of 0.98 indicates that the regression line is an excellent fit. Combination MCS 6-27 (capture mAb) and MCS 92-32 (detector mAb) was the most sensitive mAb pair, L.O.D.~30 pg/mL, (FIG. 6B). This same antibody pair gave a L.O.D. in a electrochemiluminescent ELISA or approximately 2 pg/mL (FIG. 6).

Detection of BoNT/B in Milk Matrices

MCS 6-27 and SS 92-32-10-1 as capture/detector were useful as a sensitive sandwich ELISA to detect BoNT/B. The L.O.D. and L.O. in a sandwich ELISA were 23 pg/mL and 33 pg/mL respectively and the L.O.D in a sandwich ELISA using electrochemiluminescent detection was approximately 2 pg/mL. The advantages of a mAb/mAb sandwich ELISA are many including greater reagent stability and assay reproducibility. Using the same criteria for the MCS 6-27/polyclonal assay, the L.O.D. and L.O.Q. for the mAb/mAb The sandwich ELISA described above was used to measure BoNT/B toxin recovery from spiked milk samples (skim, 2% and whole milk). Although several strategies to defat the milk prior to the ELISA were evaluated, it was found that no defatting or dilution process was required for any of the milk types. Recovery of BoNT/B from the spiked milk samples is reported in Table 3. Toxin recovery ranged from 80.4% to 106.7% at BoNT/B spike concentrations from 20,000 to 39 pg/mL. An electrochemiluminescent ELISA using MCS 6-27 and MCS 92-32-10-1 as capture/detector was able to detect BoNT/B equally well in whole milk, and buffer at all concentrations greater than 2.4 pg/mL (the lowest level tested).

TABLE 4

| Percentage recovery of BoNT/B from milk as determined by monoclonal/polyclonal sandwich ELISA. | | | | | | | |
|---|---|---|---|---|---|---|---|
| | Spike level (pg/ml) | | | | | | |
| | 20000 | 5000 | 1250 | 313 | 156 | 78 | 39 |
| Skim milk | 98.5 ± 5.7 | 108.4 ± 4.7 | 92.3 ± 2.6 | 100.5 ± 6.9 | 103.2 ± 3.6 | 94.1 ± 8.5 | 101.8 ± 13.7 |
| 2% milk | 106.2 ± 3.5 | 102.4 ± 3.7 | 101.7 ± 2.0 | 85.7 ± 2.1 | 106.7 ± 0.3 | 86.5 ± 1.6 | 80.4 ± 12.1 |
| Whole milk | 100.9 ± 3.7 | 94.0 ± 2.2 | 99.2 ± 4.5 | 97.0 ± 3.6 | 100.6 ± 5.3 | 84.9 ± 4.6 | 82.5 ± 10.3 |

1. A method for detecting BoNT/A according to claim 5 wherein said sample is aqueous, biological, environmental or a food product.
2. A method for capturing BoNT/B from a sample, said method comprising contacting said sample with the monoclonal of claim 1 or 3 and isolating the complex formed between the BoNT/A in the sample and the monoclonal antibody.

What is claimed is:

1. An isolated and purified monoclonal antibody produced by the continuous hybridoma cell line having deposit accession number ATCC PTA-11872.

2. A composition comprising the monoclonal antibody of claim 1.

* * * * *

```
                          SEQUENCE LISTING


<160> NUMBER OF SEQ ID NOS: 56

<210> SEQ ID NO 1
<211> LENGTH: 137
<212> TYPE: PRT
<213> ORGANISM: Clostridium botulinum

<400> SEQUENCE: 1

Met Ala Val Leu Gly Leu Leu Phe Cys Leu Leu Thr Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Leu Ser Leu
        35                  40                  45

Thr Asn Tyr Gly Val Ser Trp Val Arg Gln Pro Pro Gly Lys Gly Leu
    50                  55                  60

Glu Trp Leu Gly Ile Ile Trp Gly Asp Gly Ser Thr Ser Tyr His Ser
65                  70                  75                  80

Ala Leu Thr Ser Arg Leu Ser Ile Ser Lys Asp Asn Ser Lys Ser Gln
                85                  90                  95

Val Phe Leu Thr Leu Asn Ser Leu Gln Thr Asp Asp Thr Ala Thr Tyr
            100                 105                 110

Tyr Cys Ala Thr Ala Tyr Tyr Gly Tyr Thr Leu Phe Ala Tyr Trp Gly
        115                 120                 125

Gln Gly Thr Leu Val Thr Val Ser Ala
    130                 135


<210> SEQ ID NO 2
<211> LENGTH: 76
<212> TYPE: PRT
<213> ORGANISM: Clostridium botulinum

<400> SEQUENCE: 2

Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Phe Gln Gln Lys Pro Gly Gln Pro Pro
        35                  40                  45

Lys Val Leu Ile Tyr Ala Ala Ser Asn Val Glu Ser Gly Val Pro Ala
```

50 55 60

Arg Phe Ser Gly Ser Gly Ser Gly Thr Glu Phe Ser
65 70 75

<210> SEQ ID NO 3
<211> LENGTH: 78
<212> TYPE: PRT
<213> ORGANISM: Clostridium botulinum

<400> SEQUENCE: 3

Asp Ile Val Leu Thr Gln Ser Pro Ser Ser Leu Ala Val Ser Val Gly
1 5 10 15

Glu Lys Val Thr Met Ser Cys Lys Ser Ser Gln Ser Leu Leu Tyr Ser
20 25 30

Ser Asn Gln Lys Asn Tyr Leu Thr Trp Tyr Gln Gln Lys Pro Gly Gln
35 40 45

Ser Pro Lys Leu Leu Ile Tyr Trp Ala Ser Ile Arg Glu Ser Gly Val
50 55 60

Pro Asp Arg Phe Thr Gly Ser Gly Ser Gly Thr Asp Phe Thr
65 70 75

<210> SEQ ID NO 4
<211> LENGTH: 76
<212> TYPE: PRT
<213> ORGANISM: Clostridium botulinum

<400> SEQUENCE: 4

Asp Ile Val Ile Thr Gln Thr Pro Ala Ser Leu Ala Val Ser Leu Gly
1 5 10 15

Gln Arg Ala Thr Ile Ser Cys Arg Ala Ser Glu Ser Ile Asn Tyr Tyr
20 25 30

Gly Thr Asn Leu Leu Gln Trp Tyr Gln Gln Lys Pro Gly Gln Pro Pro
35 40 45

Lys Leu Leu Ile Tyr Ala Ala Ser Asn Val Glu Ser Gly Val Pro Ala
50 55 60

Arg Phe Ser Gly Ser Gly Ser Gly Thr Asp Phe Ser
65 70 75

<210> SEQ ID NO 5
<211> LENGTH: 108
<212> TYPE: PRT
<213> ORGANISM: Clostridium botulinum
<220> FEATURE:
<221> NAME/KEY: misc_feature
<222> LOCATION: (54)..(54)
<223> OTHER INFORMATION: X = Y/S
<220> FEATURE:
<221> NAME/KEY: misc_feature
<222> LOCATION: (56)..(56)
<223> OTHER INFORMATION: X = Y/S
<220> FEATURE:
<221> NAME/KEY: misc_feature
<222> LOCATION: (94)..(94)
<223> OTHER INFORMATION: X = S/T
<220> FEATURE:
<221> NAME/KEY: misc_feature
<222> LOCATION: (97)..(97)
<223> OTHER INFORMATION: X = P/L

<400> SEQUENCE: 5

Gly Asp Ile Val Met Thr Gln Ser His Lys Phe Met Ser Thr Ser Val
1 5 10 15

Gly Asp Arg Val Ser Ile Thr Cys Lys Ala Ser Gln Asp Val Ser Thr

```
            20                  25                  30

Thr Val Ala Trp Tyr Gln Gln Lys Pro Gly Gln Ser Pro Lys Leu Leu
        35                  40                  45

Ile Tyr Ser Ala Ser Xaa Arg Xaa Thr Gly Val Pro Asp Arg Phe Thr
    50                  55                  60

Gly Ser Gly Ser Gly Thr Asp Phe Thr Phe Thr Ile Ser Ser Val Gln
65                  70                  75                  80

Ala Glu Asp Leu Ala Val Tyr Tyr Cys Gln Gln His Tyr Xaa Thr Pro
                85                  90                  95

Xaa Thr Phe Gly Gly Gly Thr Lys Leu Glu Ile Lys
            100                 105


<210> SEQ ID NO 6
<211> LENGTH: 64
<212> TYPE: PRT
<213> ORGANISM: Clostridium botulinum

<400> SEQUENCE: 6

Val Thr Pro Phe Cys Ile Cys Gly Arg Tyr Val Thr Ile Thr Cys Arg
1               5                   10                  15

Ala Ser Gln Asn Ile Tyr Ser His Leu Thr Trp Phe Gln Gln Arg Gln
            20                  25                  30

Gly Arg Ser Pro Gln Leu Leu Val Tyr Thr Ala Thr Asn Leu Ala Asp
        35                  40                  45

Gly Val Pro Ala Arg Phe Ser Gly Ser Gly Ser Gly Thr Gln Tyr Ser
    50                  55                  60


<210> SEQ ID NO 7
<211> LENGTH: 69
<212> TYPE: PRT
<213> ORGANISM: Clostridium botulinum

<400> SEQUENCE: 7

His Phe Ser Ile Leu Ser Leu Trp Arg Ser Val Ser Ile Ser Cys Arg
1               5                   10                  15

Thr Ser Gln Ser Leu Val Asn Asn Lys Gly Asn Thr Tyr Leu Ser Trp
            20                  25                  30

Tyr Leu His Lys Pro Gly Gln Ser Pro Gln Leu Leu Ile Tyr Gly Ile
        35                  40                  45

Ser Asn Arg Phe Ser Gly Val Pro Asp Arg Phe Ser Gly Ser Gly Ser
    50                  55                  60

Gly Thr Asp Phe Thr
65


<210> SEQ ID NO 8
<211> LENGTH: 69
<212> TYPE: PRT
<213> ORGANISM: Clostridium botulinum

<400> SEQUENCE: 8

Glu Pro Ser Leu Ala Val Ser Leu Gly Gln Arg Ala Thr Ile Ser Cys
1               5                   10                  15

Arg Ala Ser Glu Ser Val Asp Ser Tyr Gly Asn Ser Phe Met His Trp
            20                  25                  30

Tyr Gln Gln Lys Pro Gly Gln Pro Pro Lys Leu Leu Ile Tyr Arg Ala
        35                  40                  45

Ser Asn Leu Gln Ser Gly Ile Pro Ala Arg Phe Ser Gly Ser Gly Ser
    50                  55                  60
```

-continued

```
Arg Thr Asp Phe Thr
65


<210> SEQ ID NO 9
<211> LENGTH: 68
<212> TYPE: PRT
<213> ORGANISM: Clostridium botulinum

<400> SEQUENCE: 9

Glu Pro Ser Leu Ala Val Ser Leu Gly Gln Arg Ala Thr Ile Ser Cys
1               5                   10                  15

Arg Ala Ser Glu Ser Val Asp Ser Tyr Gly Asn Ser Phe Met His Trp
            20                  25                  30

Tyr Gln Gln Lys Pro Gly Gln Pro Pro Lys Leu Leu Ile Tyr Arg Ala
        35                  40                  45

Ser Asn Leu Gln Ser Gly Ile Pro Ala Arg Ser Gly Ser Gly Ser Arg
    50                  55                  60

Thr Asp Phe Thr
65


<210> SEQ ID NO 10
<211> LENGTH: 44
<212> TYPE: PRT
<213> ORGANISM: Clostridium botulinum

<400> SEQUENCE: 10

Leu Lys Ile Ser Arg Val Glu Ala Glu Asp Leu Gly Val Tyr Phe Cys
1               5                   10                  15

Ser Gln Ser Thr His Val Pro Tyr Thr Phe Gly Gly Gly Thr Lys Leu
            20                  25                  30

Glu Ile Lys Arg Ala Asp Ala Ala Pro Thr Val Ser
        35                  40


<210> SEQ ID NO 11
<211> LENGTH: 44
<212> TYPE: PRT
<213> ORGANISM: Clostridium botulinum

<400> SEQUENCE: 11

Leu Asn Ile His Pro Val Glu Glu Asp Asp Ile Ala Met Tyr Phe Cys
1               5                   10                  15

Gln Gln Ser Arg Lys Val Pro Tyr Thr Phe Gly Gly Gly Thr Lys Leu
            20                  25                  30

Glu Ile Lys Arg Ala Asp Ala Ala Pro Thr Val Ser
        35                  40


<210> SEQ ID NO 12
<211> LENGTH: 43
<212> TYPE: PRT
<213> ORGANISM: Clostridium botulinum

<400> SEQUENCE: 12

Leu Ile Ile Ser Ser Val Lys Ala Glu Asp Leu Ala Val Tyr Tyr Cys
1               5                   10                  15

His Gln Tyr Phe Gly Tyr His Thr Phe Gly Gly Gly Thr Lys Leu Glu
            20                  25                  30

Ile Lys Arg Ala Asp Ala Ala Pro Thr Val Ser
        35                  40
```

<210> SEQ ID NO 13
<211> LENGTH: 44
<212> TYPE: PRT
<213> ORGANISM: Clostridium botulinum

<400> SEQUENCE: 13

```
Leu Asn Ile His Pro Val Glu Glu Asp Asp Ile Ala Met Tyr Phe Cys
1               5                   10                  15

Gln Gln Ser Arg Lys Val Pro Phe Thr Phe Gly Ser Gly Thr Arg Leu
            20                  25                  30

Glu Ile Lys Arg Ala Asp Ala Ala Pro Thr Val Ser
        35                  40
```

<210> SEQ ID NO 14
<211> LENGTH: 44
<212> TYPE: PRT
<213> ORGANISM: Clostridium botulinum

<400> SEQUENCE: 14

```
Leu Lys Ile Asn Ser Leu Gln Ser Glu Asp Phe Gly Ile Tyr Phe Cys
1               5                   10                  15

Gln His Phe Trp Gly Thr Pro Trp Thr Phe Gly Gly Gly Thr Lys Leu
            20                  25                  30

Glu Ile Lys Arg Ala Asp Ala Ala Pro Thr Val Ser
        35                  40
```

<210> SEQ ID NO 15
<211> LENGTH: 44
<212> TYPE: PRT
<213> ORGANISM: Clostridium botulinum

<400> SEQUENCE: 15

```
Leu Lys Ile Asn Asn Leu Gln Ser Glu Asp Phe Gly Thr Tyr Tyr Cys
1               5                   10                  15

Gln His Phe Trp Gly Thr Pro Trp Thr Phe Gly Gly Gly Thr Lys Leu
            20                  25                  30

Glu Ile Lys Arg Ala Asp Ala Ala Pro Thr Val Ser
        35                  40
```

<210> SEQ ID NO 16
<211> LENGTH: 44
<212> TYPE: PRT
<213> ORGANISM: Clostridium botulinum

<400> SEQUENCE: 16

```
Leu Lys Ile Ser Thr Ile Lys Pro Glu Asp Leu Gly Met Tyr Tyr Cys
1               5                   10                  15

Phe Gln Gly Thr His Gln Pro Phe Thr Phe Gly Ala Gly Thr Lys Leu
            20                  25                  30

Glu Leu Lys Arg Ala Asp Ala Ala Pro Thr Val Ser
        35                  40
```

<210> SEQ ID NO 17
<211> LENGTH: 38
<212> TYPE: PRT
<213> ORGANISM: Clostridium botulinum

<400> SEQUENCE: 17

```
Leu Thr Ile Asn Pro Val Glu Ala Asp Asp Val Ala Thr Tyr Tyr Cys
1               5                   10                  15

Gln Gln Ser Asn Glu Asp Pro His Ser Asp Arg Asn Arg Ala Thr Asn
```

```
            20                  25                  30

Leu Lys Arg Thr Glu Met
        35


<210> SEQ ID NO 18
<211> LENGTH: 38
<212> TYPE: PRT
<213> ORGANISM: Clostridium botulinum

<400> SEQUENCE: 18

Leu Thr Ile Asn Pro Val Glu Ala Asp Asp Val Ala Thr Tyr Tyr Cys
1               5                   10                  15

Gln Gln Ser Asn Glu Asp Pro His Ser Asp Arg Asn Arg Ala Thr Asn
            20                  25                  30

Leu Lys Arg Thr Glu Met
        35


<210> SEQ ID NO 19
<211> LENGTH: 58
<212> TYPE: PRT
<213> ORGANISM: Clostridium botulinum

<400> SEQUENCE: 19

Glu Val Lys Leu Glu Glu Ser Gly Gly Gly Leu Val Lys Leu Gly Gly
1               5                   10                  15

Ser Leu Lys Leu Ser Cys Ala Val Ser Gly Phe Thr Phe Ser Ser Tyr
            20                  25                  30

Tyr Met Ser Trp Val Arg Gln Thr Pro Glu Lys Arg Leu Glu Leu Val
        35                  40                  45

Ala Ala Ile Lys Ser Asn Gly Asp Asn Thr
    50                  55


<210> SEQ ID NO 20
<211> LENGTH: 58
<212> TYPE: PRT
<213> ORGANISM: Clostridium botulinum

<400> SEQUENCE: 20

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ile Phe Thr Asn Tyr
            20                  25                  30

Trp Met His Trp Val Lys Gln Arg Pro Gly Gln Gly Leu Glu Trp Ile
        35                  40                  45

Gly Glu Ile Asn Pro Thr Asn Gly Arg Thr
    50                  55


<210> SEQ ID NO 21
<211> LENGTH: 58
<212> TYPE: PRT
<213> ORGANISM: Clostridium botulinum

<400> SEQUENCE: 21

Glu Val Lys Leu Gln Glu Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45
```

Gly Glu Ile Leu Pro Gly Ser Gly Ser Thr
    50                  55

<210> SEQ ID NO 22
<211> LENGTH: 58
<212> TYPE: PRT
<213> ORGANISM: Clostridium botulinum

<400> SEQUENCE: 22

Glu Val Gln Leu Glu Glu Ser Gly Pro Glu Leu Val Lys Pro Gly Thr
1               5                   10                  15

Ser Val Lys Ile Ser Cys Lys Ala Ser Gly Tyr Ser Phe Thr Gly Tyr
            20                  25                  30

Ile Ile Asn Trp Val Met Gln Ser Gln Gly Lys Thr Pro Glu Trp Ile
        35                  40                  45

Gly Arg Ile Asn Pro Asn Asn Gly Asp Thr
    50                  55

<210> SEQ ID NO 23
<211> LENGTH: 58
<212> TYPE: PRT
<213> ORGANISM: Clostridium botulinum

<400> SEQUENCE: 23

Glu Val Gln Leu Glu Gln Ser Gly Pro Gly Leu Val Lys Pro Ser Gln
1               5                   10                  15

Ser Leu Ser Leu Thr Cys Thr Val Thr Gly Tyr Ser Ile Thr Asn Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Thr Thr
    50                  55

<210> SEQ ID NO 24
<211> LENGTH: 58
<212> TYPE: PRT
<213> ORGANISM: Clostridium botulinum

<400> SEQUENCE: 24

Glu Val Lys Leu Glu Glu Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Gly Trp Val Lys Glu Arg Pro Gly His Gly Leu Glu Trp Ile
        35                  40                  45

Gly Asp Ile Phe Pro Gly Gly Gly Phe Thr
    50                  55

<210> SEQ ID NO 25
<211> LENGTH: 60
<212> TYPE: PRT
<213> ORGANISM: Clostridium botulinum

<400> SEQUENCE: 25

Gln Val Thr Leu Lys Glu Ser Gly Pro Gly Val Leu Gln Pro Ser Gln
1               5                   10                  15

Thr Leu Ser Leu Thr Cys Ser Phe Ser Gly Phe Ser Leu Asn Thr Ser
            20                  25                  30

Asn Val Val Val Asn Trp Ile Arg Gln Pro Ser Gly Lys Asp Leu Glu
        35                  40                  45

```
Trp Leu Ala His Ile Trp Trp Asp Asn Asp Lys Ala
    50                  55                  60


<210> SEQ ID NO 26
<211> LENGTH: 57
<212> TYPE: PRT
<213> ORGANISM: Clostridium botulinum

<400> SEQUENCE: 26

Tyr Tyr Ser Asp Thr Val Lys Gly Arg Phe Thr Ile Ser Arg Asp Asn
1               5                   10                  15

Ala Lys Asn Thr Leu Tyr Leu Gln Met Ser Ser Leu Lys Ser Glu Asp
            20                  25                  30

Thr Ala Phe Tyr Tyr Cys Ala Arg Phe Asn Ser Gly Ser Ser Trp Phe
        35                  40                  45

Asp Tyr Trp Gly Gln Gly Thr Leu Val
    50                  55


<210> SEQ ID NO 27
<211> LENGTH: 52
<212> TYPE: PRT
<213> ORGANISM: Clostridium botulinum

<400> SEQUENCE: 27

Asn Gln Asn Glu Lys Phe Lys Ser Lys Ala Thr Leu Thr Val Asp Lys
1               5                   10                  15

Ser Ser Ser Thr Ala His Met Gln Leu Ser Ser Leu Thr Ser Glu Asp
            20                  25                  30

Ser Ala Val Tyr Tyr Cys Ala Arg Arg Gly Phe Gly Asn Trp Gly Gln
        35                  40                  45

Gly Thr Thr Leu
    50


<210> SEQ ID NO 28
<211> LENGTH: 53
<212> TYPE: PRT
<213> ORGANISM: Clostridium botulinum

<400> SEQUENCE: 28

Asn Asn Asn Glu Lys Phe Lys Gly Lys Ala Thr Phe Thr Ala Asp Ser
1               5                   10                  15

Ser Ser Asn Thr Val Tyr Met Gln Leu Ser Ser Leu Thr Ser Glu Asp
            20                  25                  30

Ser Ala Val Tyr Tyr Cys Ala Arg Leu Asp Val Met Asp Tyr Trp Gly
        35                  40                  45

Gln Gly Thr Ser Val
    50


<210> SEQ ID NO 29
<211> LENGTH: 52
<212> TYPE: PRT
<213> ORGANISM: Clostridium botulinum

<400> SEQUENCE: 29

Ser Tyr Asn Gln Lys Phe Lys Gly Lys Ala Thr Leu Thr Val Asp Arg
1               5                   10                  15

Ser Ser Ser Thr Ala His Met Glu Val Arg Ser Leu Thr Ser Glu Asp
            20                  25                  30

Ser Ala Val Tyr Tyr Cys Ala Arg Thr Gly Phe Gly Tyr Trp Gly Gln
```

```
        35                  40                  45

Gly Thr Leu Val
    50


<210> SEQ ID NO 30
<211> LENGTH: 52
<212> TYPE: PRT
<213> ORGANISM: Clostridium botulinum

<400> SEQUENCE: 30

Ser Tyr Asn Pro Ser Leu Lys Ser Arg Ile Ser Ile Thr Arg Asp Thr
1               5                   10                  15

Ser Lys Asn Gln Phe Phe Leu Gln Phe Asn Ser Val Thr Thr Glu Asp
            20                  25                  30

Thr Ala Thr Tyr Tyr Cys Ala Arg Ser Pro Leu Ala Tyr Trp Gly Gln
        35                  40                  45

Gly Thr Leu Val
    50


<210> SEQ ID NO 31
<211> LENGTH: 59
<212> TYPE: PRT
<213> ORGANISM: Clostridium botulinum
<220> FEATURE:
<221> NAME/KEY: misc_feature
<222> LOCATION: (10)..(24)
<223> OTHER INFORMATION: Noncoding Region

<400> SEQUENCE: 31

Asn Tyr Asn Glu Asn Phe Lys Gly Lys Ala Thr Leu Thr Ala Asp Thr
1               5                   10                  15

Ser Ser Ser Pro Ala Tyr Met Gln Leu Ser Ser Met Thr Ser Glu Asp
            20                  25                  30

Ser Ser Ile Tyr His Cys Ala Arg Gly Arg Gly His Asn Ser Ser Thr
        35                  40                  45

Tyr Phe Asp Ser Trp Gly Gln Gly Thr Thr Leu
    50                  55


<210> SEQ ID NO 32
<211> LENGTH: 51
<212> TYPE: PRT
<213> ORGANISM: Clostridium botulinum

<400> SEQUENCE: 32

Tyr Lys Ser Val Arg Gly Asp Gln Phe Pro Arg Ile Pro Pro Ala Thr
1               5                   10                  15

Arg Tyr Ser Ser Thr Ser Pro Met Trp Thr Leu Arg Ile Leu Pro His
            20                  25                  30

Thr Thr Val Leu Glu Cys Leu His Thr Leu Asp Tyr Trp Gly Gln Gly
        35                  40                  45

Thr Ser Ser
    50


<210> SEQ ID NO 33
<211> LENGTH: 14
<212> TYPE: PRT
<213> ORGANISM: Clostidium botulinum

<400> SEQUENCE: 33

Thr Val Ser Ala Ala Lys Thr Thr Pro Pro Ser Val Tyr Arg
1               5                   10
```

<210> SEQ ID NO 34
<211> LENGTH: 13
<212> TYPE: PRT
<213> ORGANISM: Clostridium botulinum

<400> SEQUENCE: 34

Thr Val Ser Ser Glu Ser Ala Arg Asn Pro Thr Ile Arg
1 5 10

<210> SEQ ID NO 35
<211> LENGTH: 14
<212> TYPE: PRT
<213> ORGANISM: Clostridium Botulinum

<400> SEQUENCE: 35

Thr Val Ser Ser Ala Lys Thr Thr Pro Pro Ser Val Tyr Arg
1 5 10

<210> SEQ ID NO 36
<211> LENGTH: 14
<212> TYPE: PRT
<213> ORGANISM: Clostridium Botulinum

<400> SEQUENCE: 36

Thr Val Ser Ala Ala Lys Thr Thr Pro Pro Ser Val Tyr Arg
1 5 10

<210> SEQ ID NO 37
<211> LENGTH: 14
<212> TYPE: PRT
<213> ORGANISM: Clostridium Botulinum

<400> SEQUENCE: 37

Thr Val Ser Ala Ala Lys Thr Thr Pro Pro Ser Val Tyr Arg
1 5 10

<210> SEQ ID NO 38
<211> LENGTH: 4
<212> TYPE: PRT
<213> ORGANISM: Clostridium Botulinum

<400> SEQUENCE: 38

Thr Ser Pro Ala
1

<210> SEQ ID NO 39
<211> LENGTH: 4
<212> TYPE: PRT
<213> ORGANISM: Clostridium Botulinum

<400> SEQUENCE: 39

Pro Ser Ala Gln
1

<210> SEQ ID NO 40
<211> LENGTH: 40
<212> TYPE: PRT
<213> ORGANISM: Clostridium Botulinum

<400> SEQUENCE: 40

Gly Gly Ala Thr Cys Cys Ala Thr Gly Cys Cys Ala Gly Thr Thr Ala
1 5 10 15

Cys Ala Ala Thr Ala Ala Ala Thr Ala Ala Thr Thr Thr Thr Ala Ala

```
            20                  25                  30

Thr Thr Ala Thr Ala Ala Thr Gly
        35                  40


<210> SEQ ID NO 41
<211> LENGTH: 42
<212> TYPE: PRT
<213> ORGANISM: Clostridium botulinum

<400> SEQUENCE: 41

Cys Thr Cys Gly Ala Gly Thr Thr Ala Thr Thr Thr Ala Ala Cys Ala
1               5                   10                  15

Cys Thr Thr Thr Thr Ala Cys Ala Cys Ala Thr Thr Thr Gly Thr Ala
            20                  25                  30

Thr Cys Thr Thr Ala Thr Ala Thr Ala Cys
        35                  40


<210> SEQ ID NO 42
<211> LENGTH: 26
<212> TYPE: PRT
<213> ORGANISM: Clostridium botulinum

<400> SEQUENCE: 42

Gly Gly Ala Thr Cys Cys Gly Cys Ala Ala Gly Thr Ala Thr Ala Thr
1               5                   10                  15

Thr Thr Ala Ala Thr Ala Gly Ala Cys Gly
            20                  25


<210> SEQ ID NO 43
<211> LENGTH: 27
<212> TYPE: PRT
<213> ORGANISM: Clostridium botulinum

<400> SEQUENCE: 43

Cys Thr Cys Gly Ala Gly Thr Thr Ala Gly Cys Cys Thr Thr Thr Gly
1               5                   10                  15

Thr Thr Thr Thr Cys Thr Thr Gly Ala Ala Cys
            20                  25


<210> SEQ ID NO 44
<211> LENGTH: 31
<212> TYPE: PRT
<213> ORGANISM: Clostridium botulinum

<400> SEQUENCE: 44

Gly Gly Ala Thr Cys Cys Gly Cys Thr Cys Cys Ala Gly Gly Ala Ala
1               5                   10                  15

Thr Ala Thr Gly Thr Ala Thr Thr Gly Ala Thr Gly Thr Thr Gly
            20                  25                  30


<210> SEQ ID NO 45
<211> LENGTH: 32
<212> TYPE: PRT
<213> ORGANISM: Clostridium botulinum

<400> SEQUENCE: 45

Cys Thr Cys Gly Ala Gly Thr Thr Ala Thr Thr Cys Ala Gly Thr Cys
1               5                   10                  15

Cys Ala Cys Cys Cys Thr Thr Cys Ala Thr Cys Thr Thr Thr Ala Gly
            20                  25                  30
```

<210> SEQ ID NO 46
<211> LENGTH: 33
<212> TYPE: PRT
<213> ORGANISM: Clostridium botulinum

<400> SEQUENCE: 46

```
Cys Thr Cys Gly Ala Gly Thr Thr Ala Gly Cys Thr Ala Thr Thr Ala
1               5                   10                  15

Thr Ala Thr Thr Thr Ala Thr Thr Ala Ala Ala Cys Ala Thr Thr Thr
            20                  25                  30

Cys
```

<210> SEQ ID NO 47
<211> LENGTH: 38
<212> TYPE: PRT
<213> ORGANISM: Clostridium botulinum

<400> SEQUENCE: 47

```
Gly Gly Ala Thr Cys Cys Gly Ala Ala Ala Thr Thr Thr Thr Ala Ala
1               5                   10                  15

Ala Thr Ala Ala Thr Ala Thr Thr Ala Thr Cys Thr Thr Ala Ala Ala
            20                  25                  30

Thr Thr Thr Ala Ala Gly
        35
```

<210> SEQ ID NO 48
<211> LENGTH: 32
<212> TYPE: PRT
<213> ORGANISM: Clostridium botulinum

<400> SEQUENCE: 48

```
Cys Thr Cys Gly Ala Gly Thr Thr Ala Gly Cys Thr Ala Thr Ala Thr
1               5                   10                  15

Gly Ala Thr Thr Gly Ala Ala Thr Thr Thr Thr Ala Thr Ala Thr Cys
            20                  25                  30
```

<210> SEQ ID NO 49
<211> LENGTH: 29
<212> TYPE: PRT
<213> ORGANISM: Clostridium botulinum

<400> SEQUENCE: 49

```
Gly Gly Ala Thr Cys Cys Gly Ala Ala Thr Ala Thr Thr Thr Ala Ala
1               5                   10                  15

Ala Ala Gly Ala Thr Thr Thr Thr Thr Gly Gly Gly Gly
            20                  25
```

<210> SEQ ID NO 50
<211> LENGTH: 16
<212> TYPE: PRT
<213> ORGANISM: Clostridium botulinum

<400> SEQUENCE: 50

```
Gly Thr Ala Ala Ala Ala Cys Gly Ala Cys Gly Gly Cys Cys Ala Gly
1               5                   10                  15
```

<210> SEQ ID NO 51
<211> LENGTH: 17
<212> TYPE: PRT
<213> ORGANISM: Clostridium botulinum

<400> SEQUENCE: 51

-continued

```
Cys Ala Gly Gly Ala Ala Ala Cys Ala Gly Cys Thr Ala Thr Gly Ala
1               5                   10                  15

Cys


<210> SEQ ID NO 52
<211> LENGTH: 30
<212> TYPE: PRT
<213> ORGANISM: Clostridium botulinum

<400> SEQUENCE: 52

Cys Ala Ala Thr Ala Gly Ala Thr Ala Ala Thr Gly Cys Thr Thr Thr
1               5                   10                  15

Ala Ala Cys Thr Ala Ala Ala Ala Gly Ala Ala Ala Thr Gly
            20                  25                  30


<210> SEQ ID NO 53
<211> LENGTH: 22
<212> TYPE: PRT
<213> ORGANISM: Clostridium botulinum

<400> SEQUENCE: 53

Gly Thr Gly Thr Thr Cys Thr Ala Thr Cys Thr Ala Thr Ala Thr Cys
1               5                   10                  15

Ala Cys Cys Ala Thr Cys
            20


<210> SEQ ID NO 54
<211> LENGTH: 24
<212> TYPE: PRT
<213> ORGANISM: Clostridium botulinum

<400> SEQUENCE: 54

Cys Ala Ala Ala Thr Thr Gly Ala Thr Ala Ala Gly Thr Ala Cys Thr
1               5                   10                  15

Thr Gly Ala Ala Ala Thr Cys Cys
            20


<210> SEQ ID NO 55
<211> LENGTH: 19
<212> TYPE: PRT
<213> ORGANISM: Clostridium botulinum

<400> SEQUENCE: 55

Gly Cys Thr Ala Gly Thr Thr Ala Thr Thr Gly Cys Thr Cys Ala Gly
1               5                   10                  15

Ala Gly Gly


<210> SEQ ID NO 56
<211> LENGTH: 20
<212> TYPE: PRT
<213> ORGANISM: Clostridium botulinum

<400> SEQUENCE: 56

Glu Glu Arg Tyr Lys Ile Gln Ser Tyr Ser Glu Tyr Leu Lys Asp Phe
1               5                   10                  15

Trp Gly Asn Pro
            20
```